(12) United States Patent
Yoo et al.

(10) Patent No.: US 9,670,817 B2
(45) Date of Patent: Jun. 6, 2017

(54) SYSTEMS AND METHODS FOR RUNNING A NOX SELF-DIAGNOSTIC TEST

(71) Applicant: Ford Global Technologies, LLC, Dearborn, MI (US)

(72) Inventors: In Kwang Yoo, Ann Arbor, MI (US); Michiel J. Van Nieuwstadt, Ann Arbor, MI (US); Garth Michael Meyer, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 10 days.

(21) Appl. No.: 14/739,834

(22) Filed: Jun. 15, 2015

(65) Prior Publication Data

US 2016/0363030 A1    Dec. 15, 2016

(51) Int. Cl.
*F01N 3/00* (2006.01)
*F01N 11/00* (2006.01)
*F01N 3/20* (2006.01)

(52) U.S. Cl.
CPC .......... *F01N 11/00* (2013.01); *F01N 3/2066* (2013.01); *F01N 2570/14* (2013.01)

(58) Field of Classification Search
CPC ..... F01N 3/2066; F01N 11/00; F01N 2570/14
USPC .......................................................... 60/277
See application file for complete search history.

(56) References Cited

U.S. PATENT DOCUMENTS 8,694,197 B2    4/2014  Rajagopalan
2014/0144126 A1    5/2014  Kowalkowski et al.

*Primary Examiner* — Jason Shanske
(74) *Attorney, Agent, or Firm* — Julia Voutyras; McCoy Russell LLP

(57) ABSTRACT

Methods and systems are provided for detecting NOx sensor degradation based on results from a NOx sensor self-diagnostic (SD) test. In one example, a method may comprise: determining that a nitrogen oxide (NOx) sensor is degraded if outputs received from the sensor via a CAN bus during a self-diagnostic test are outside a threshold range. Additionally, only outputs received from the sensor during a self-diagnostic (SD) test performed after a first completed SD test after a key-off event, where the outputs are generated under conditions where a temperature at the sensor is less than a threshold, and an oxygen concentration is within a threshold range may be used to determine if the sensor is degraded.

20 Claims, 7 Drawing Sheets

SYSTEMS AND METHODS FOR RUNNING A NOX SELF-DIAGNOSTIC TEST

TECHNICAL FIELD

The present application relates to the control of emissions in vehicle exhaust systems.

BACKGROUND AND SUMMARY

Selective catalytic reduction (SCR) catalysts may be utilized in the exhaust systems of diesel engines to reduce NOx emissions. A reductant, such as urea, may be injected into the exhaust system upstream of the SCR catalyst, and together, the reductant and the SCR catalyst may chemically reduce NOx molecules to nitrogen and water, thereby limiting NOx emissions. However, if a component of the NOx emission control system, such as the SCR catalyst, becomes degraded, NOx emissions may increase. NOx sensors, configured to measure NOx levels in the exhaust system, may therefore be positioned in the exhaust system to detect failures of the NOx emission control system. Specifically, increases in NOx levels that may be indicative of degradation of one or more components of the NOx emission control system may be detected by the NOx sensors. Thus, the efficiency of the SCR catalyst, and other components of a NOx emission control system may be monitored by one or more NOx sensors positioned in the exhaust system.

NOx sensors may also become degraded, and estimations of the NOx levels may become less accurate. As a result, NOx slippage in the exhaust system may not be detected. In order to monitor the accuracy of a NOx sensor, the NOx sensor may run self-diagnostic (SD) tests after an engine key-off event where an engine is turned off. One such attempt to detect NOx sensor degradation is described in US Patent Application 2014/0144126 to Kowalkowski et al. The disclosure attempts to detect NOx sensor degradation by running one or more SD tests during an engine after-run state.

However, the inventors of the present application have recognized a problem with the above solution. In particular, the disclosed attempt does not address a significant contributor to the NOx levels estimated by the NOx sensor. As one example, urea injected into the exhaust system during engine operation, and/or urea droplets delivered to the exhaust system after the key-off event during a urea delivery line purging process, may persist in the exhaust system after the engine key-off event. Under sufficiently high exhaust temperatures, urea in the exhaust system may be converted to ammonia. NOx sensors register ammonia as NOx, and therefore NOx levels may be overestimated. Therefore, the accuracy of NOx SD tests may decrease with increasing exhaust temperatures and urea concentrations in the exhaust system.

The inventors herein have devised systems and methods for addressing the issues described above. In one example, the issues described above may be addressed by a method comprising: determining that a nitrogen oxide (NOx) sensor is degraded based on outputs received from the sensor via a CAN bus during a self-diagnostic (SD) test performed after a first completed SD test after a key-off event, only if the outputs are generated under conditions where a temperature at the sensor is less than a threshold, a NOx concentration is less than a threshold, and an oxygen concentration is within a threshold range.

In another representation, the issues described above may be addressed by a method comprising: excluding a first completed self-diagnostic (SD) test result of an NOx sensor after an engine key-off event, excluding test results from a completed SD test if one or more of an exhaust gas temperature is greater than a threshold, an oxygen concentration of the exhaust gas is outside a threshold range, and a NOx concentration of the exhaust gas is higher than a threshold, otherwise not excluding test results from a completed SD test, and determining that the sensor is degraded only if the non-excluded test results are different from a reference value by more than a threshold.

In this way, by excluding SD test results from SD tests where the exhaust gas temperature is greater than a threshold, and/or the NOx concentration is greater than a threshold, the variance in the SD test results may be reduced. Said another way, the accuracy of the SD test results may be improved. As such, the sensitivity for distinguishing a degraded NOx sensor from a NOx sensor that is not degraded may be increased. Therefore, the efficiency of a NOx emission control system in an exhaust system may be increased.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to systems and methods for performing a NOx sensor self-diagnostic (SD) test and determining if a NOx sensor is degraded based on results from the SD test. The exhaust systems of diesel engines, such as the engine system shown in FIG. 1, and exhaust system shown in FIG. 1B, may comprise a selective catalytic reduction (SCR) catalyst for reducing NOx emissions. The efficiency of the SCR catalyst may be monitored by one or more NOx sensors positioned upstream and/or downstream of the SCR catalyst. An example NOx sensor is shown below with reference to FIG. 2.

Figure 4:
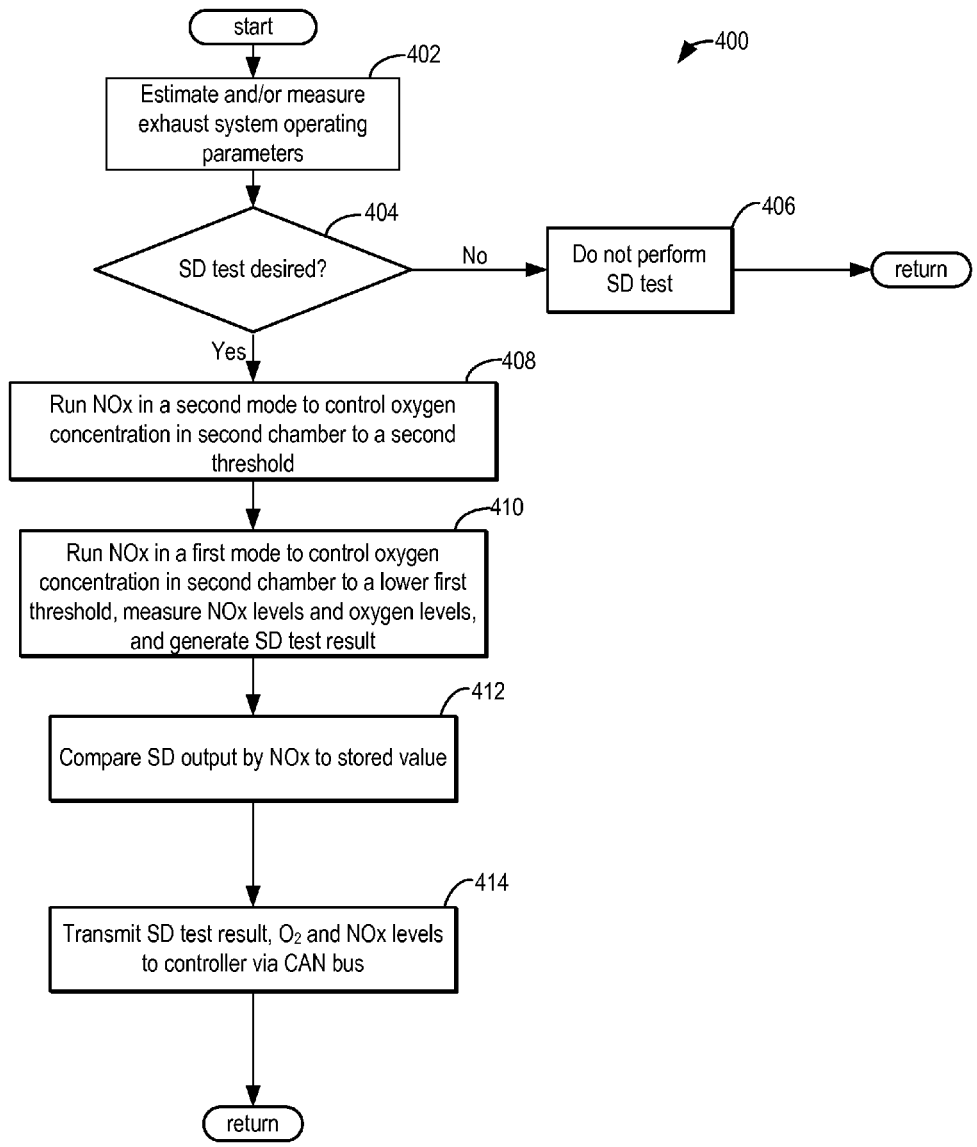
FIG. 4 shows a flow chart of an example method for performing a self-diagnostic (SD) test on a NOx sensor.

However, the NOx sensor may become degraded (e.g., gain-skewed) over use, and thus NOx sensors may run self-diagnostic (SD) tests to monitor the accuracy of their outputs. An example method for running a SD test is shown in FIG. 4. Outputs from the SD test may vary depending on the concentration of ammonia in the exhaust gas, as ammonia may be registered as NOx by the NOx sensors. Ammonia concentration in the exhaust gas may increase with increases in an amount of urea and/or exhaust gas temperatures. As such, outputs from the SD test may become increasingly divergent with increasing exhaust gas temperature and/or urea concentration. Therefore, outputs from a NOx sensor that is not degraded, and outputs from a NOx sensor that is degraded may overlap, and thus, a NOx sensor that is degraded may not be identified.

Figure 5:
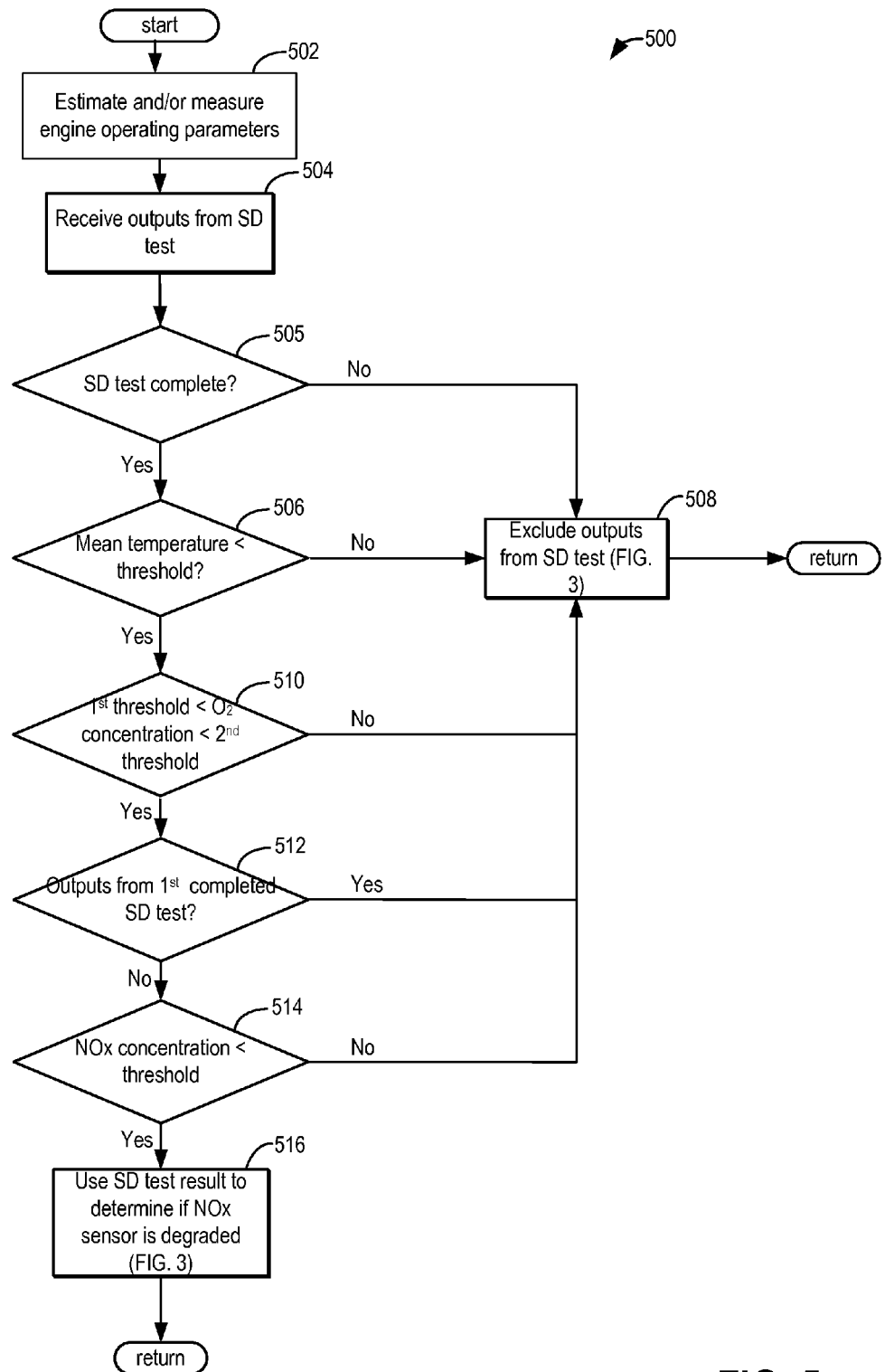
FIG. 5 shows a flow chart of an example method for excluding outputs from a NOx sensor during a SD test to detect a gain skewed-low type of sensor degradation.
Figure 6:
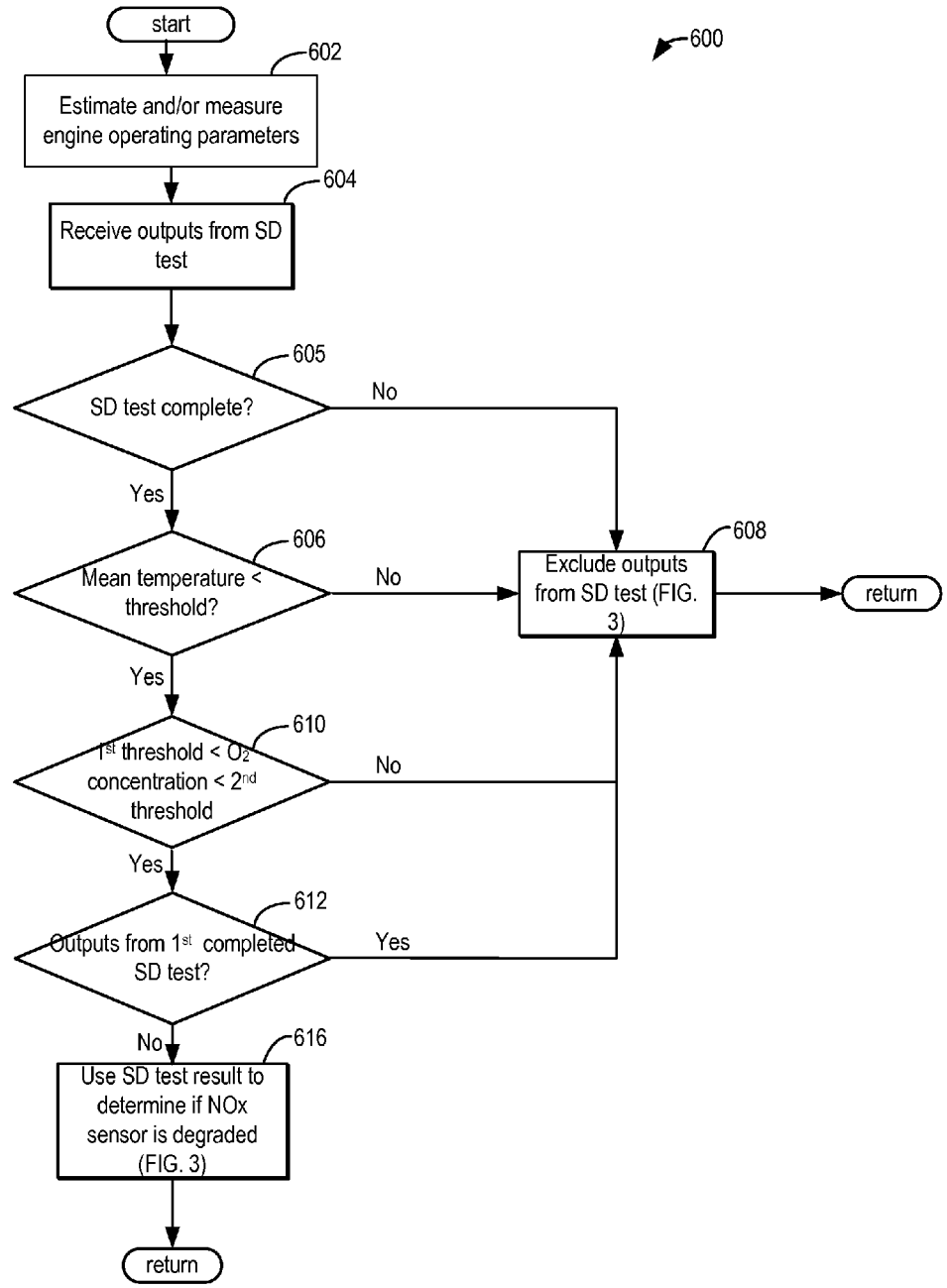
FIG. 6 shows a flow chart of an example method for excluding outputs from a NOx sensor during a SD test to detect a gain skewed-high type of sensor degradation.

FIGS. 5-6, show example methods for excluding outputs from SD test results where the exhaust gas temperature is above a threshold, the oxygen concentration is above a threshold, etc. In this way, the variance, or spread of results from the SD tests may be reduced. After excluding SD test results based on one or more of exhaust gas temperature, NOx concentration, oxygen concentration, and an order in which the SD tests were run, a method such as the example method shown in FIG. 3, may be executed to determine if the NOx sensor is degraded. In this way, a NOx that is degraded may be identified even if exhaust temperatures and/or urea levels in the exhaust system fluctuate.

Figure 1A:
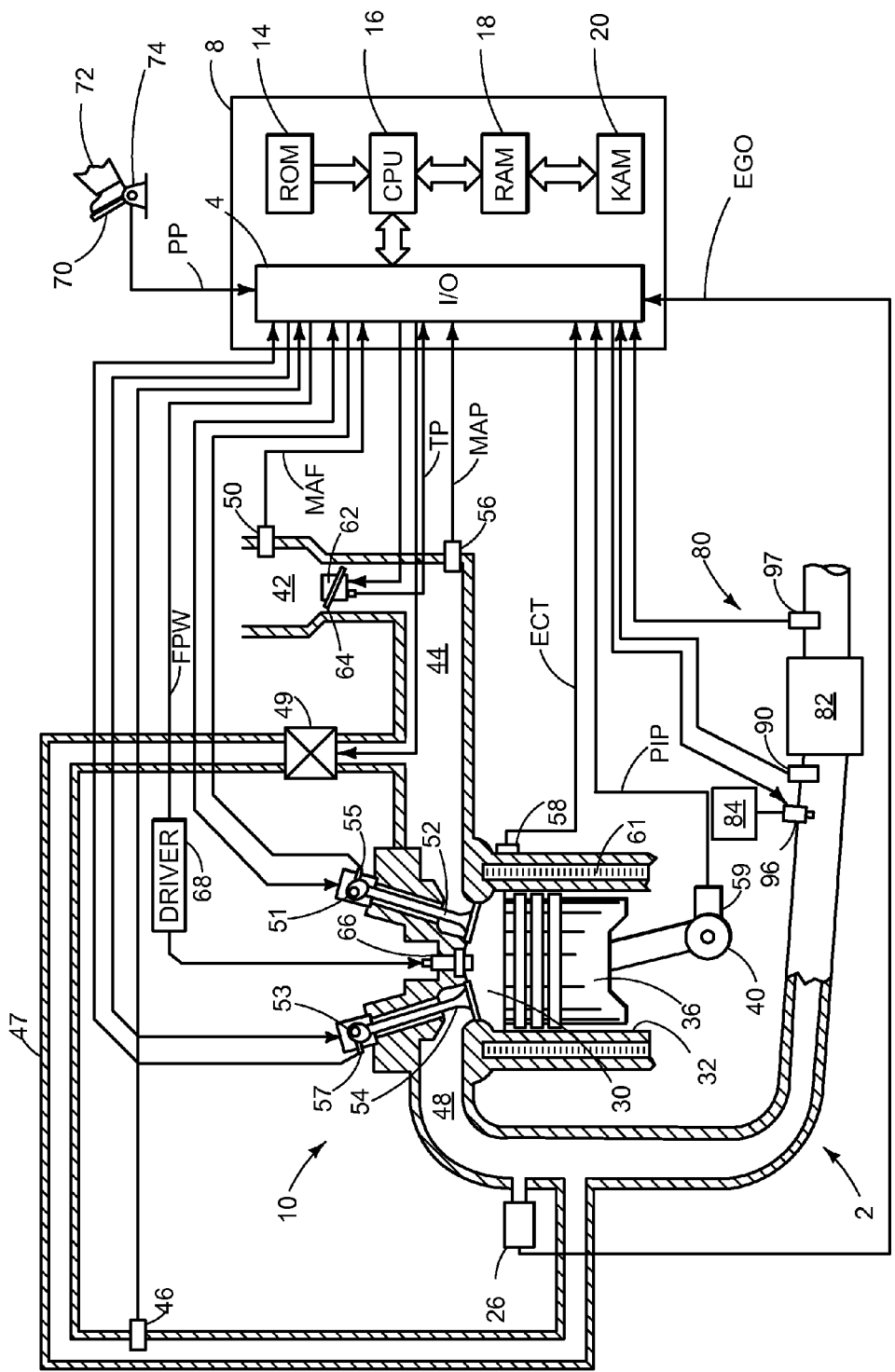
FIG. 1A shows a schematic diagram of an engine including an exhaust system with an exhaust gas treatment system.

Referring now to FIG. 1A, a schematic diagram showing one cylinder of a multi-cylinder engine 10, which may be included in a propulsion system of an automobile, is illustrated. The engine 10 may be controlled at least partially by a control system including a controller 8 and by input from a vehicle operator 72 via an input device 70. In this example, the input device 70 includes an accelerator pedal and a pedal position sensor 74 for generating a proportional pedal position signal PP. A combustion chamber (i.e., cylinder) 30 of the engine 10 may include combustion chamber walls 32 with a piston 36 positioned therein. The piston 36 may be coupled to a crankshaft 40 so that reciprocating motion of the piston is translated into rotational motion of the crankshaft. The crankshaft 40 may be coupled to at least one drive wheel of a vehicle via an intermediate transmission system. Further, a starter motor may be coupled to the crankshaft 40 via a flywheel to enable a starting operation of the engine 10.

The combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via respective intake valve 52 and exhaust valve 54. In some embodiments, the combustion chamber 30 may include two or more intake valves and/or two or more exhaust valves.

In the example depicted in FIG. 1A, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 8 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. The fuel injector 66 is shown coupled directly to the cylinder 30 for injecting fuel directly therein in proportion to the pulse width of signal FPW received from the controller 8 via an electronic driver 68. In this manner, the fuel injector 66 provides what is known as direct injection (hereafter also referred to as "DI") of fuel into the combustion cylinder 30.

It will be appreciated that in an alternate embodiment, the injector 66 may be a port injector providing fuel into the intake port upstream of the cylinder 30. It will also be appreciated that the cylinder 30 may receive fuel from a plurality of injectors, such as a plurality of port injectors, a plurality of direct injectors, or a combination thereof.

In one example, the engine 10 is a diesel engine that combusts air and diesel fuel through compression ignition. In other non-limiting embodiments, the engine 10 may combust a different fuel including gasoline, biodiesel, or an alcohol containing fuel blend (e.g., gasoline and ethanol or gasoline and methanol) through compression ignition and/or spark ignition.

The intake passage 42 may include a throttle 62 having a throttle plate 64. In this particular example, the position of the throttle plate 64 may be varied by the controller 8 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 8 by throttle position signal TP. The intake passage 42 may include a mass air flow sensor 50 and a manifold air pressure sensor 56 for providing respective signals, MAF and MAP, to the controller 8.

Further, in the disclosed embodiments, an exhaust gas recirculation (EGR) system may route a desired portion of exhaust gas from the exhaust passage 48 to the intake passage 42 via an EGR passage 47. The amount of EGR provided to the intake manifold 44 may be varied by a controller 8 via an EGR valve 49. By introducing exhaust gas to the engine 10, the amount of available oxygen for combustion is decreased, thereby reducing combustion flame temperatures and reducing the formation of $NO_x$ for example. As depicted, the EGR system further includes an EGR sensor 46 which may be arranged within the EGR passage 47 and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

An exhaust system 2 includes an exhaust gas sensor 26 coupled to the exhaust passage 48 upstream of an exhaust gas treatment system 80. The sensor 26 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. The exhaust gas treatment system 80 is shown arranged along the exhaust passage 48 downstream of the exhaust gas sensor 26.

In the example shown in FIG. 1A, the exhaust gas treatment system 80 is a urea based selective catalytic reduction (SCR) system. The SCR system includes at least a reduction catalyst (herein, SCR catalyst 82), a reductant storage tank (herein, urea storage reservoir 84), and a reductant injector (herein, urea injector 96), for example. In other embodiments, the exhaust gas treatment system 80 may additionally or alternatively include other components, such as a particulate filter, lean $NO_x$ trap, three way catalyst, various other emission control devices, or combinations thereof. For example, urea injector 96 may be positioned upstream of reduction catalyst 82 and downstream of an oxidation catalyst. In the depicted example, the urea injector 96 provides urea from the urea storage reservoir 84. However, various alternative approaches may be used, such as solid urea pellets that generate an ammonia vapor, which is then injected or metered to the SCR catalyst 82. In still another example, a lean $NO_x$ trap may be positioned upstream of the SCR catalyst 82 to generate $NH_3$ for the SCR catalyst 82, depending on the degree or richness of the air-fuel ratio fed to the lean $NO_x$ trap.

The exhaust gas treatment system 80 further includes a tailpipe exhaust gas sensor 97 positioned downstream of the SCR catalyst 82. In the depicted embodiment, tailpipe exhaust gas sensor 97 may be a $NO_x$ sensor, for example, for measuring an amount of post-SCR $NO_x$ released via the tailpipe of exhaust passage 48. Exhaust gas treatment system 80 may further include a feedgas exhaust gas sensor 90 positioned upstream of the SCR catalyst 82 and downstream of urea injector 96. In the depicted embodiment, the feedgas exhaust gas sensor 90 may also be a $NO_x$ sensor, for example, for measuring an amount of pre-SCR $NO_x$ received in the exhaust passage for treatment at the SCR catalyst.

In some examples, an efficiency of the SCR system may be determined based on the output of one or more of tailpipe exhaust gas sensor 97 and feedgas exhaust gas sensor 90. For example, the SCR system efficiency may be determined by comparing $NO_x$ levels upstream of the SCR catalyst (via sensor 90) with $NO_x$ levels downstream of the SCR catalyst (via sensor 97). The efficiency may be further based on the exhaust gas sensor 26 (when the sensor 26 measures $NO_x$, for example) positioned upstream of the SCR system. In other examples, exhaust gas sensors 97, 90, and 26 may be any suitable sensor for determining an exhaust gas constituent concentration, such as a UEGO, EGO, HEGO, HC, CO sensor, etc.

The controller 8 is shown in FIG. 1A as a microcomputer, including a microprocessor unit 16, input/output ports 4, an electronic storage medium for executable programs and calibration values shown as a read only memory chip 14 in this particular example, random access memory 18, keep alive memory 20, and a data bus. The controller 8 may be in communication with and, therefore, receive various signals from sensors coupled to the engine 10, in addition to those signals previously discussed, including measurement of inducted mass air flow (MAF) from the mass air flow sensor 50; engine coolant temperature (ECT) from a temperature sensor 58 coupled to a cooling sleeve 61; a profile ignition pickup signal (PIP) from a Hall effect sensor 59 (or other type) coupled to the crankshaft 40; throttle position (TP) from a throttle position sensor; absolute manifold pressure signal, MAP, from the sensor 56; and exhaust constituent concentration from the exhaust gas sensors 26, 90, and 97. An engine speed signal, RPM, may be generated by the controller 8 from signal PIP.

The storage medium read-only memory 14 can be programmed with non-transitory, computer readable data representing instructions executable by the processor 16 for performing the methods described below as well as other variants that are anticipated but not specifically listed. Example methods are described herein with reference to FIGS. 3-4.

As described above, FIG. 1A shows only one cylinder of a multi-cylinder engine, and each cylinder may similarly include its own set of intake/exhaust valves, fuel injector, spark plug, etc.

Figure 1B:
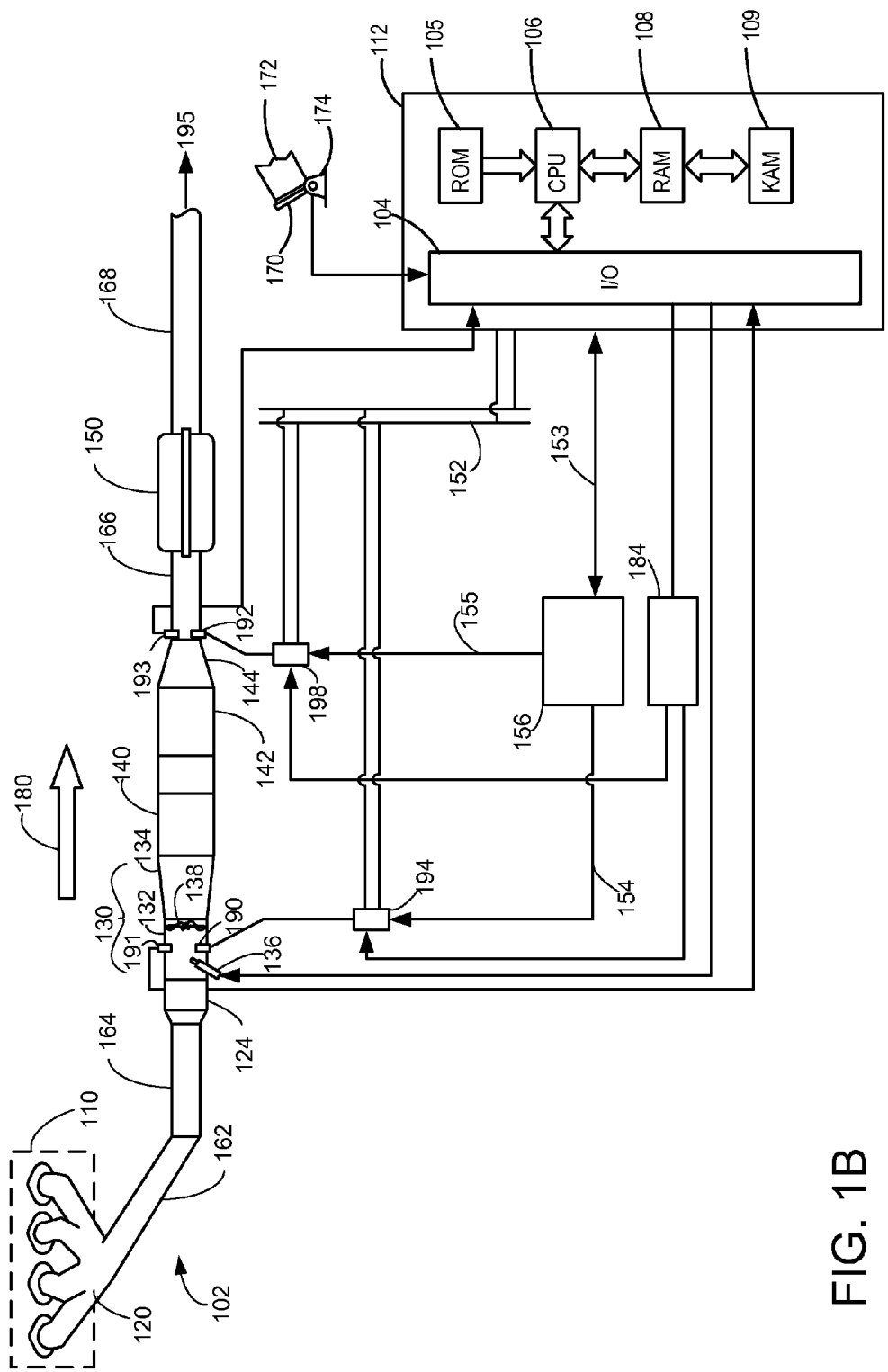
FIG. 1B illustrates an exhaust system for receiving engine exhaust gas.

FIG. 1B illustrates a schematic view of an example exhaust system 102 of a vehicle system for transporting exhaust gases produced by internal combustion engine 110. Exhaust system 102 may be exhaust system 2 of FIG. 1A, for example. As one non-limiting example, engine 110 includes a diesel engine that produces a mechanical output by combusting a mixture of air and diesel fuel. Alternatively, engine 110 may include other types of engines such as gasoline burning engines, among others.

Exhaust system 102 may include one or more of the following: an exhaust manifold 120 for receiving exhaust gases produced by one or more cylinders of engine 110, an oxidation catalyst 124, mixing region 130, selective catalytic reductant (SCR) catalyst 140, emission control device 142, and noise suppression device 150. Additionally, exhaust system 102 may include a plurality of exhaust pipes or passages for fluidically coupling the various exhaust system components of exhaust system 102. It is important to note that one or more of the oxidation catalyst 124, mixing region 130, SRC catalyst 140, emission control device 142, and noise suppression device 150 may be arranged in any order or combination in the exhaust system 102.

However, as shown the example of FIG. 1B, exhaust manifold 120 may be fluidically coupled to oxidation catalyst 124 by one or more of first exhaust passage 162 and second exhaust passage 164. As, such oxidation catalyst 124 may be downstream of exhaust manifold 120, with no additional components separating the oxidation catalyst 124 from the exhaust manifold 120 other than one or more of the exhaust passages 162 and 164. In the description herein, the flow of gasses and/or fluids in the exhaust system 102 may be in a direction away from exhaust manifold 120, towards surrounding environment 195, through the exhaust system 102, and out of the exhaust system 102 through passage 168. Thus, in the example shown in FIG. 1B, the flow of gasses and/or fluids in the exhaust system 102 may generally be from left to right as indicated by flow arrow 180. Therefore, in the description herein, downstream may be used to refer to the relative positioning of components in the exhaust system 102 with respect to the flow direction in the exhaust system 102. As such, if a first component is described as downstream relative to a second component in the exhaust system 102, then gasses and/or fluids flowing in the exhaust system 102 may flow through the second component before flowing through first component.

Returning now to FIG. 1B, one or more of the first exhaust passage 162 and second exhaust passage 164 may provide fluidic communication between the exhaust manifold 120 and the oxidation catalyst. In some example the oxidation catalyst 120 may be a diesel oxidation catalyst (DOC). The DOC may be an exhaust flow through device that includes a honey-comb formed substrate having a large surface area coated with a catalyst layer. The catalyst layer may include precious metals including, but not limited to, platinum and palladium. As the exhaust flows over the catalyst layer, carbon monoxide, gaseous hydrocarbons and liquid hydrocarbon particles may be oxidized to reduce emissions.

The mixing region 130 may be arranged immediately downstream of oxidation catalyst 124 for receiving a liquid reductant, with no additional components separating the mixing region 130 from the oxidation catalyst 124. The mixing region 130 may include a first mixing region 132, and a second mixing region 134, where the second mixing region 134 is downstream of the first mixing region 132. The first mixing region 132 may include an injector 136, for injecting a liquid into the mixing region 130. In some examples, the liquid injected by the injector 136, may be a liquid reductant such as ammonia or urea. The liquid reductant may be supplied by to the injector 136 from a storage tank (not shown). Further, the injector 136 may comprise an electronically actuated valve. In such examples, the injector 136 may be in electrical and/or electronic communication with controller 112, for receiving signals from the controller 112. As such, controller 112, may send electronic signals to the injector 136, for adjusting a position of the valve of the injector. In response to signals received from the controller 112, an actuator of the injector 136 may adjust the position of the valve of the injector 136, to adjust an amount of liquid reductant being injected to the mixing region 130.

Additionally, the first mixing region 132 may comprise an upstream first nitrogen oxide (NOx) sensor 190, and an upstream first temperature sensor 191. The positioning of the first NOx sensor 190 and the first temperature sensor 191 in the exhaust system 102 may be such that the NOx sensor 190 and temperature sensor 191 are superposed. Said another way, the first NOx sensor 190 and the first temperature sensor 191 may be approximately aligned with, and may coincide with one another in the exhaust system 102. Said another way, the NOx sensor 190 and temperature sensor 191 may be radially arranged along a cross section of the flow path of exhaust gasses in the exhaust system 102. In some examples, the NOx sensor 190 and the first temperature sensor 191, may be arranged perpendicular to the flow of gasses and/or fluid in the exhaust system 102, and in such examples, may further be positioned in the exhaust system 102 so that they are parallel to one another. In other examples, the temperature sensor 191 may be positioned directly adjacent to the NOx sensor 190, so that the temperature sensor 191 and NOx sensor 190 are in face-sharing contact with one another. In this way, gasses and/or fluids flowing through the exhaust system 102, and more specifically through first mixing region 132, may flow past the first NOx sensor 190 and the first temperature sensor 191 at approximately the same time. As such, the first temperature sensor 191 may be positioned within the first mixing region 132 for measuring a temperature of gasses and/or fluids flowing past and/or being sampled at the first NOx sensor 190.

However, in other examples, the temperature sensor 191 may not be aligned with the NOx sensor 190. Thus, the temperature sensor 191 may be positioned adjacent to the NOx sensor 190, and/or may be spaced away from the NOx sensor 190.

The temperature sensor 191 may be electrically coupled to the controller 112, where outputs of the temperature sensor 191 corresponding to a temperature of gasses and/or fluids flowing past the NOx sensor 190 may be sent to the controller 112. In some examples, the first NOx sensor 190 and first temperature sensor 191 may be positioned downstream of the injector 136 as shown in FIG. 1B. However, in other examples, the first NOx sensor 190 and first temperature sensor 191, may be positioned substantially in line with injector 136. In still further examples, the NOx sensor 190 and temperature sensor 191 may be positioned upstream of the injector 136.

The second mixing region 134 of mixing region 130 may be configured to accommodate a change in cross-sectional area or flow area between the first mixing region 132 and the catalyst 140. Specifically, the cross-sectional flow area created by the second mixing region 134 may increase in a downstream direction. As such, catalyst 140 may be positioned downstream of mixing region 130. Therefore, the first NOx sensor 190, and the first temperature sensor 191 are positioned upstream of the SCR catalyst 140. In some examples, no additional components may separate the second mixing region 134 from the SCR catalyst 140. In some examples, a mixing device 138 may be included in the exhaust system 120 and may be arranged downstream of injector 136. Mixing device 138 may be configured to receive engine exhaust gas and/or injected fluid reductant from injector 136 from upstream of the mixing device 138 and direct the engine exhaust gas and/or fluid reductant downstream of the mixing device 138 towards the SCR catalyst 140. As shown in FIG. 1B, mixing device 138 may comprise a circular disc of fin sections. Each fin section may have a straight edge and a curved edge. In some examples, the mixing device 138 may be positioned in the first mixing region 132 downstream of the injector 136, temperature sensor 191, and NOx sensor 190. In other examples, the mixing device 138 may be positioned in the second mixing region 134. The mixing device 138, may increase the commingling and therefore uniformity of the exhaust gas and/or fluid reductant mixture in the second mixing region 134 before the mixture reaches the SCR catalyst 140.

The SCR device 140 is configured to convert NOx gasses into water and nitrogen as inert byproducts of combustion using the fluid reductant, e.g., ammonia (NH3) or urea, injected by the injector 136 and an active catalyst. The catalyst, often referred to as a DeNOx catalyst, may be constructed of titanium dioxide containing the oxides of transition metals such as, for example, vanadium, molybdenum, and tungsten to act as catalytically active components. The SCR device 124 may be configured as a ceramic brick or a ceramic honeycomb structure, a plate structure, or any other suitable design. Note that catalyst 140 can include any suitable catalyst for reducing NOx or other products of combustion resulting from the combustion of fuel by engine 110.

The emission control device 142 may be positioned downstream of the SCR catalyst 140. In some examples, the emission control device 142 may be a diesel particulate filter (DPF). The DPF may operate actively or passively, and the filtering medium can be of various types of material and geometric construction. One example construction includes a wall-flow ceramic monolith comprising alternating channels that are plugged at opposite ends, thus forcing the exhaust flow through the common wall of the adjacent channels whereupon the particulate matter is deposited.

While in the example shown in FIG. 1B the SCR catalyst 140 is upstream of the emission control device 142, in other examples, the emission control device 142 may be positioned upstream of the SCR catalyst 140. However, in all such examples, the first NOx sensor 190 and the first temperature sensor 191 are positioned upstream of the SCR catalyst 140 and the emission control device 142.

Still in further examples, it is possible that the emission control device 142 and the SCR catalyst 140 may be combined on one substrate (e.g., a wall-flow ceramic DPF element coated with NOx storage agents and platinum group metals).

After passing through the emission control device 142, exhaust gasses and/or fluids may continue through an after-treatment region 144. The after-treatment region 144 may be configured to accommodate a change in cross-sectional area or flow area between the emission control device 142 and third exhaust passage 166. Specifically, the cross-sectional flow area created by the after-treatment mixing region 144 may decrease in a downstream direction. Thus, the after-treatment mixing region 144 may fluidically couple the emission control device 142 to the third exhaust passage 166. However, in other examples, the exhaust system 102 may not include after-treatment mixing region 144, and as such, the emission control device 142 may be directly and/or physically coupled to the third exhaust passage 166, with no additional components separating the emission control device 142 from the third exhaust passage 166.

A downstream second temperature sensor 193, and a downstream second NOx sensor 192 may be positioned in the third exhaust passage 166. However, in other examples, the second temperature sensor 193, and the second NOx sensor 192 may be positioned in the after-treatment mixing region 144. In all examples, the second temperature sensor 193, and the second NOx sensor 192 are positioned downstream of the SCR catalyst 140 and the emission control device 142. The second temperature sensor 193 and second NOx sensor 192 may be positioned within the exhaust system 102 in a similar manner to that of first temperature sensor 191 and first NOx sensor 190. As such, the second NOx sensor 192 and second temperature sensor 193 may superposed in the exhaust system 102. Said another way, the second NOx sensor 192 and the second temperature sensor 193 may be approximately aligned with, and may coincide with one another in the exhaust system 102.

Thus, in some examples, the NOx sensor 192 and the temperature sensor 193, may be arranged perpendicular to the flow of gasses and/or fluid in the exhaust system 102, and in such examples, may further be positioned in the exhaust system 102 so that they are parallel to one another. In this way, gasses and/or fluids flowing through the exhaust system 102, and more specifically flowing downstream of the SCR catalyst 140 and emission control device 142, may flow past the second NOx sensor 192 and the second temperature sensor 193 at approximately the same time. As such, the second temperature sensor 193 may be positioned within the exhaust system 102 for measuring a temperature of gasses and/or fluids flowing past and/or being sampled at the second NOx sensor 192. The temperature sensor 193 may be electrically coupled to the controller 112, where outputs of the temperature sensor 193 corresponding to a temperature of gasses and/or fluids flowing past and/or being sampled at the NOx sensor 192 may be sent to the controller 112.

However, in other examples, the temperature sensor 193 may not be aligned with the NOx sensor 192. Thus, the temperature sensor 193 may be positioned adjacent to the NOx sensor 191, and/or may be spaced away from the NOx sensor 192.

Noise suppression device 150 may be arranged downstream of catalyst 140 and emission control device 142. Noise suppression device 150 may be configured to attenuate the intensity of sound waves traveling away from exhaust manifold 120, towards surrounding environment 195. Third exhaust passage 166 may provide fluidic communication between after-treatment region 144 and noise suppression device 150. Thus, exhaust gases may be permitted to flow from the after-treatment region 144, through third exhaust passage 166, to noise suppression device 150. After passing through noise suppression device 150, exhaust gasses may flow through fourth exhaust passage 168 en route to the surrounding environment 195.

Returning to the first NOx sensor 190 and second NOx sensor 192, both of the sensors 190 and 192 may be constructed and function similarly. They may both be configured to measure and/or estimate a concentration of NOx and/or $O_2$ in an exhaust gas mixture flowing through the exhaust system 102. The structure and functioning of the sensors 190 and 192 may be described in greater detail below with reference to FIG. 2.

The first NOx sensor 190 may be electrically coupled to a first NOx sensor module 194, and the second NOX sensor 192 may be electrically coupled to a second NOX sensor module 198. The vehicle system 100 may also include Controller Area Network (CAN) bus 152 in communication with the exhaust system 102 and controller 112. The CAN bus may exchange information using a scheduled periodic rate. As such, the CAN bus 152 provides electronic communication between the controller 112, and the first NOx sensor module 194 and the second NOx sensor module 198. Measurements from the two NOx sensors 190 and 192 (e.g. NOx concentration, $O_2$ concentration, etc.) are first relayed to the NOX sensor modules 194 and 198, respectively. The NOx sensor modules 194 and 198 may then convert signals received from the NOx sensors 190 and 192, respectively, into a CAN data stream, which may then be transmitted to the controller 112 via the CAN bus 152. The NOx sensor modules 194 and 198 may also include computer readable instructions stored in non-transitory memory for determining whether a self-diagnostic (SD) test is complete.

During engine operation, each of the NOx sensors 190 and 192 may operate in a first mode, as described in greater detail below with reference to FIG. 2, to measure and/or estimate NOx levels in the exhaust system 102. The upstream first NOx sensor measures NOx levels emitted by the engine 110, while the downstream second NOx sensor measures NOx levels remaining in the exhaust system 102 after treatment by the SCR catalyst 140. By comparing the outputs of the two NOx sensors 190 and 192 during engine operation, the overall NOx removal efficiency of the exhaust system 102 may be estimated.

However, the NOx sensors 190 and 192 may become degraded (e.g., gain-skewed, cracked, contaminated, etc.), and as a result the accuracy of their outputs used to estimate and/or measure NOx levels in the exhaust system 102 may become reduced. In order to detect, and diagnose NOx sensor degradation, the accuracy of a sensor's outputs may be monitored after an engine key-off event as described in greater detail below with reference to FIG. 3. Thus, in a second mode of operation, after an engine key-off event, the NOx sensors 190 and 192 may run one or more self-diagnostic (SD) tests to determine if one or more of the NOx sensors 190 and 192 are degraded. A key-off event may be determined by the controller 112 based on signals received from an input device 170. The input device 170 may include a button, switch, knob, ignition, touch screen display, etc., where the position and/or digital state of the input device 170 may be adjusted to turn the engine 110 on or off. The input device 170 may therefore in some examples by an ignition for a vehicle system with a keyed engine-on, engine-off functionality. In other embodiments, in the case of a keyless vehicle system, the start/stop and/or on/off functionality of the vehicle system may be controlled by a button, switch, knob, touch screen, etc. Thus, a vehicle operator 172, may adjust the input device 170 to a first position and/or digital state during a key-on event to turn on the engine 110. During a key-off event the vehicle operator 172, may adjust the position of the input device to a second position and/or digital state during a key-off event to turn off the engine 110. Said another way, a key-off event may be used to refer to conditions when the engine 110 is shutdown to rest and the vehicle is off (e.g., during an engine key-off and/or vehicle key-off event, or engine stop event in a keyless system with a stop/start button). Thus, the key-off event may comprise terminating a combustion cycle in the engine 110 based on input from the vehicle operator 172 via an input device. In some examples, the vehicle system 100 may additionally include a position sensor 174, for measuring a position of the input device 170. The position of the input device 170 may be transmitted to the controller 112, and may thus be used by the controller 112 to determine the occurrence of a key-off and/or key-on event.

Power to the NOx sensors 190 and 192 after an engine key-off event may in some examples be provided by a glow plug control module 156. However, in other examples, power to the NOx sensor 190 and 192 may be provided by a battery 184. Thus, in a second mode of operation, after an engine key-off event, the NOx sensors 190 and 192 may run one or more self-diagnostic (SD) tests to determine if one or more of the NOx sensor 190 and 192 are degraded. During this second mode of operation, where the NOx sensors 190 and 192 run one or more SD tests, the glow plug control module 156 and/or battery 184, may provide power to the upstream first NOx sensor 190 and the downstream second NOx sensor 192. The glow plug control module 156 and battery 184 may be in electrical communication with the controller 112, for receiving digital signals therefrom. In some examples, the glow plug control module 156, may be in communication with the controller 112 via the CAN bus 152. The controller 112 may in some examples initiate an engine after-run routine where a required amount of after-run extension time may be transmitted to the glow plug control module (GPCM) 156 via signal 143, while the engine 110 is running.

As described in greater detail below with reference to FIG. 3, the controller 112 may comprise computer readable instructions stored in non-transitory memory for initiating an engine after-run routine after a key-off event. Controller 112 may determine and transmit a desired duration (e.g. amount of time, number of SD test cycles, etc.) for the after-run routine to the glow plug control module (GPCM) 156. Thus, the desired duration may be an amount of time the after a key-off event that the GPCM 156 may continue to supply power to one or more components of the vehicle system 100, such as one or more of the NOx sensor 190 and 192. In some examples, the controller 112 may transmit the desired duration via signal 143 to the GPCM 156, while the engine 110 is running, which in some examples may be before a key-off event. However, in other examples the desired duration may be transmitted to the GPCM after a key-off event. The engine after-run routine is defined when the engine is turned off after a key-off event, but power is still supplied to the exhaust system 102 and CAN bus 152 with the GPCM 156. Further, the controller 112 may send signals to one or more of the NOx sensors 190 and 192 after a key-off event to initiate and/or run one or more SD tests.

Controller 112 is shown in FIG. 1B as a microcomputer including: microprocessor unit 106, input/output ports 104, read-only memory 105, random access memory 108, keep alive memory 109, and a conventional data bus. Controller 112 is shown receiving various signals from sensors coupled to exhaust system 102, in addition to those signals previously discussed, including: exhaust gas temperature from temperature sensors 191 and 193 which may be coupled to first mixing region 132 and third exhaust passage 166 respectively; a position sensor 174 coupled to an input device 170 for sensing input device position adjusted by a vehicle operator 172; and NOx levels from NOx sensors 190 and 192 positioned upstream and downstream of the SCR catalyst 140, respectively.

Note that with regards to vehicle applications, exhaust system 102 may be arranged on the underside of the vehicle chassis. Additionally, it should be appreciated that the exhaust system 102 may include one or more bends or curves to accommodate a particular vehicle arrangement. Further still, it should be appreciated that in some embodiments, exhaust system 102 may include additional components not illustrated in FIG. 1B and/or may omit components described herein.

Figure 2:
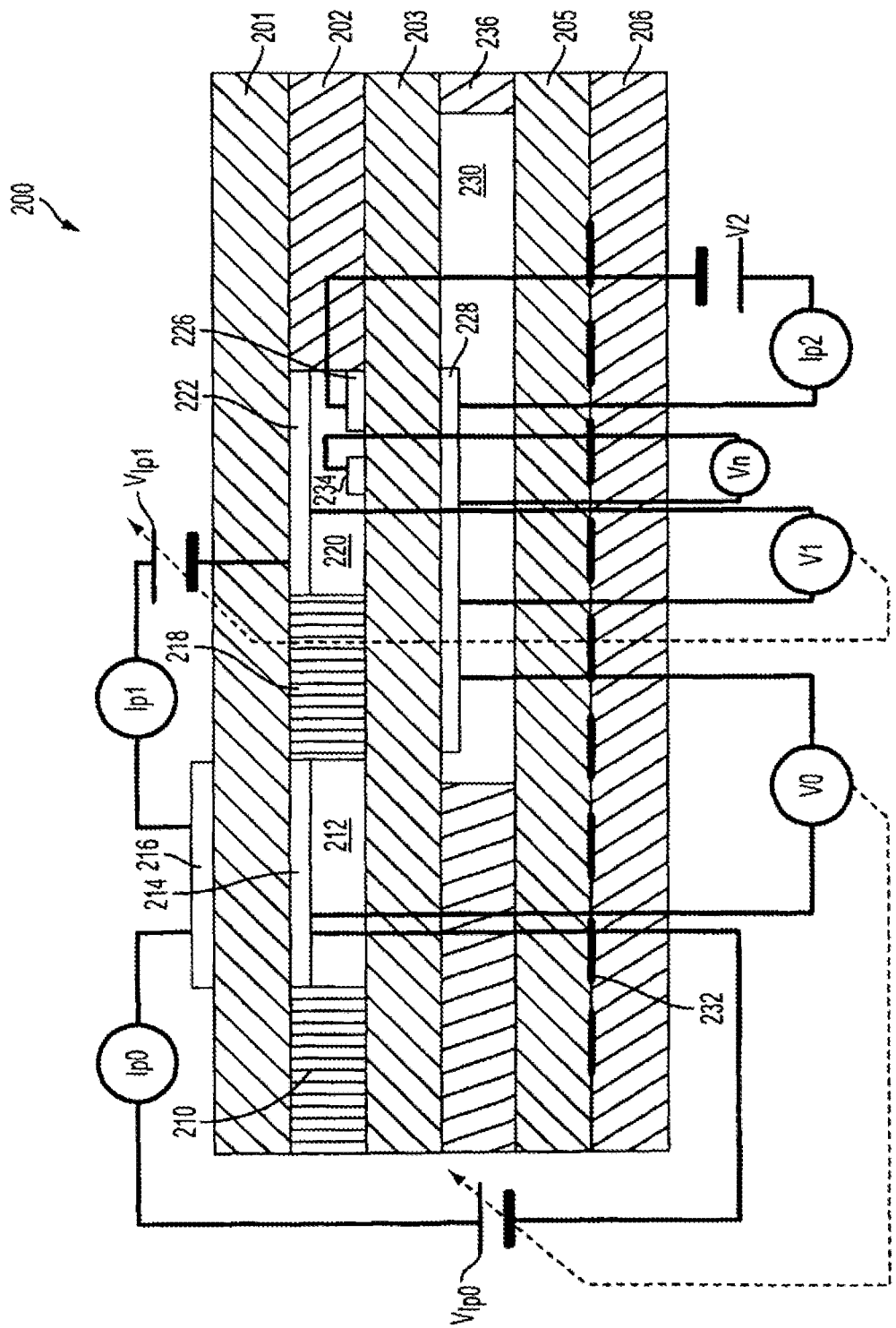
FIG. 2 shows a schematic diagram of an example NOx sensor.

FIG. 2 shows a schematic view of an example embodiment of a NOx sensor 200 configured to measure a concentration of NOx gases in an emissions stream. Sensor 200 may operate as the NOx sensor 190 or 192 of FIG. 1B, for example. Sensor 200 comprises a plurality of layers of one or more ceramic materials arranged in a stacked configuration. In the embodiment of FIG. 2, six ceramic layers are depicted as layers 201, 202, 203, 204, 205, and 206. These layers include one or more layers of a solid electrolyte capable of conducting ionic oxygen. Examples of suitable solid electrolytes include, but are not limited to, zirconium oxide-based materials. Further, in some embodiments, a heater 232 may be disposed between the various layers (or otherwise in thermal communication with the layers) to increase the ionic conductivity of the layers. While the depicted NOx sensor is formed from six ceramic layers, it will be appreciated that the NOx sensor may include any other suitable number of ceramic layers.

Layer 202 includes a material or materials creating a first diffusion path 210. First diffusion path 210 is configured to introduce exhaust gases from an exhaust passage (e.g., first mixing region 132 shown in FIG. 1B) into a first internal cavity 212 via diffusion. A first pair of pumping electrodes 214 and 216 are disposed in communication with internal cavity 212, and may be configured to electrochemically pump a selected exhaust gas constituent from internal cavity 212 through layer 201 and out of sensor 200. Generally, the species pumped from internal cavity 212 out of sensor 200 may be a species that may interfere with the measurement of a desired analyte. For example, molecular oxygen (e.g., $O_2$) can potentially interfere with the measurement of NOx in a NOx sensor, as oxygen is dissociated and pumped at a lower potential than NOx. Therefore, first pumping electrodes 214 and 216 may be used to remove molecular oxygen from within internal cavity 212 to decrease the concentration of oxygen within the sensor relative to a concentration of NOx within the sensor.

First diffusion path 210 may be configured to allow one or more components of exhaust gases, including but not limited to the analyte and interfering component, to diffuse into internal cavity 212 at a more limiting rate than the interfering component can be electrochemically pumped out by first pumping electrodes pair 214 and 216. In this manner, almost all of oxygen may be removed from first internal cavity 212 to reduce interfering effects caused by oxygen. Herein, the first pumping electrodes pair 214 and 216 may be referred to as an O2 pumping cell.

The process of electrochemically pumping the oxygen out of first internal cavity 212 includes applying an electric potential VIp0 across first pumping electrode pair 214, 216 that is sufficient to dissociate molecular oxygen, but not sufficient to dissociate NOx. With the selection of a material having a suitably low rate of oxygen diffusion for first diffusion path 210, the ionic current Ip0 between first pumping electrode pair 214, 216 may be limited by the rate at which the gas can diffuse into the chamber, which is proportional to the concentration of oxygen in the exhaust gas, rather than by the pumping rate of the O2 pumping cell. This may allow a substantial majority of oxygen to be pumped from first internal cavity 212 while leaving NOx gases in first internal cavity 212. A voltage V0 across first pumping electrode 214 and reference electrode 228 may be monitored to provide feedback control for the application of the electric potential VIp0 across first pumping electrode pair 214, 216.

Sensor 200 further includes a second internal cavity 220 separated from the first internal cavity by a second diffusion path 218. Second diffusion path 218 is configured to allow exhaust gases to diffuse from first internal cavity 212 into second internal cavity 220. A second pumping electrode 222 optionally may be provided in communication with second internal cavity 220. Second pumping electrode 222 may, in conjunction with electrode 216, be set at an appropriate potential VIp1 to remove additional residual oxygen from second internal cavity 220. Second pumping electrode 222 and electrode 216 may be referred to herein as a second pumping electrode pair or a residual O2 monitoring cell. Alternatively, second pumping electrode 222 may be configured to maintain a substantially constant concentration of oxygen within second internal cavity 220. In some embodiments, (VIp0) may be approximately equal to (VIp1) while in other embodiments (VIp0) and (VIp1) may be different. While the depicted embodiment utilizes electrode 216 to pump oxygen from first internal cavity 212 and from second internal cavity 220, it will be appreciated that a separate electrode (not shown) may be used in conjunction with electrode 222 to form an alternate pumping electrode pair to pump oxygen from second internal cavity 220. A voltage V1 across second pumping electrode 222 and reference electrode 228 may be monitored to provide feedback control for the application of the electric potential VIp1 across second pumping electrode pair 222, 216.

First pumping electrode 212 and second pumping electrode 222 may be made of various suitable materials. In some embodiments, first pumping electrode 212 and second pumping electrode may be at least partially made of a material that catalyzes the dissociation of molecular oxygen to the substantial exclusion of NOx. Examples of such materials include, but are not limited to, electrodes containing platinum and/or gold.

Sensor 200 further includes a measuring electrode 226 and a reference electrode 228. Measuring electrode 226 and reference electrode 228 may be referred to herein as a measuring electrode pair. Reference electrode 228 is disposed at least partially within or otherwise exposed to a reference duct 230. In one embodiment, reference duct 230 may be open to the atmosphere and may be referred to as a reference air duct. In another embodiment, reference duct 230 may be isolated by a layer 236 from the atmosphere such that oxygen pumped from second internal cavity 220 may be accumulated within the duct, thus reference duct 230 may be referred to as an oxygen duct.

Measuring electrode 226 may be set at a sufficient potential relative to reference electrode 228 to pump NOx out of second internal cavity 220. Further, measuring electrode 226 may be at least partially made of a material that catalyzes dissociation or reduction of any NOx. For example, measuring electrode 226 may be made at least partially from platinum and/or rhodium. As NOx is reduced to N2, the oxygen ions generated are electrochemically pumped from second internal cavity 220. The sensor output is based upon the pumping current flowing through measuring electrode 226 and reference electrode 228, which is proportional to the concentration of NOx in second internal cavity 220. Thus, the pair of electrodes 226 and 228 may be referred to herein as a NOx pumping cell.

Sensor 200 further includes a calibration electrode 234. Calibration electrode 234 is used to measure the residual oxygen concentration in second internal cavity 220 according to a Nernst voltage (Vn) with reference to reference electrode 228. Thus, calibration electrode 234 and reference electrode 228 may be referred to herein as a calibration electrode pair or as a residual O2 monitoring cell. As shown in FIG. 2, calibration electrode 234 is disposed on the same solid electrolyte layer 203 as measuring electrode 226. Typically, calibration electrode 234 is disposed spatially adjacent to measuring electrode 226. The term "spatially adjacent" as used herein refers to the calibration electrode 234 being in the same volume of space (for example, second internal cavity 220) as measuring electrode 226. Furthermore, placing the calibration electrode 234 in close proximity to measuring electrode 226 may reduce the magnitude of any differences in oxygen concentration at the measuring electrode and at the calibration electrode due to an oxygen concentration gradient between the two electrodes. This may allow residual oxygen concentrations to be measured more accurately. Alternatively, calibration electrode 234 and measuring electrode 226 may be disposed on different solid electrolyte layers. For example, calibration electrode 234 may be disposed on solid electrolyte layer 201 instead of layer 203.

It will be appreciated that the depicted calibration electrode locations and configurations are merely exemplary, and that calibration electrode 234 may have various suitable locations and configurations that allows a measurement of residual oxygen to be obtained. Further, while the depicted embodiment utilizes electrode 228 as a reference electrode of the calibration electrode pair, it will be appreciated that a separate electrode (not shown) may be used in conjunction with calibration electrode 234 to form an alternative calibration electrode pair configuration.

It should be appreciated that the NOx sensors described herein are merely example embodiments of NOx sensors, and that other embodiments of NOx sensors may have additional and/or alternative features and/or designs. For example, in some embodiments, a NOx sensor may include only one diffusion path and one internal cavity, thereby placing the first pumping electrode and measuring electrode in the same internal cavity. In such an embodiment, a calibration electrode may be disposed adjacent to the measuring electrode so that the residual oxygen concentration of an exhaust gas at or near the measuring electrode can be determined with a minimized impact from any oxygen concentration gradient.

In a first mode of operation, where the NOx concentration may be estimated and/or measured, the electric potential applied across the second pumping electrode pair, may be greater than the electric potential applied across the first pumping electrode pair. In some examples, VIp0 may be approximately 425 mV and VIp1 may be approximately 450 mV. VIp1 may be controlled to a constant voltage to regulate the concentration of $O_2$ in the second internal cavity 220. Thus, VIp1 is regulated in the first mode of operation to maintain the oxygen concentration in the second internal cavity 220 to a lower first level. In some examples the first level of $O_2$ may be approximately $10^{-3}$ ppm. Measuring electrode 226 may be set at a sufficient potential relative to reference electrode 228 to pump NOx out of second internal cavity 220. As NOx is reduced to N2, the oxygen ions generated are electrochemically pumped from second internal cavity 220. The sensor output is based upon the pumping current flowing through measuring electrode 226 and reference electrode 228, which in the first mode of operation may be proportional to the concentration of NOx in second internal cavity 220.

During a second mode of operation, VIp1 may be controlled to maintain the oxygen concentration in the second internal cavity to a higher second level. In some examples, the second level of $O_2$ may be approximately 1000 ppm. Measuring electrode 226 may be set at a sufficient potential relative to reference electrode 228 to pump $O_2$ out of second internal cavity 220. The sensor output is based upon the pumping current flowing through measuring electrode 226 and reference electrode 228, which in the second mode of operation may be proportional to the concentration of $O_2$ in second internal cavity 220.

As explained below with reference to FIG. 4, after an engine key-off event, the NOx sensor may run one or more SD tests. Each test may comprise operating the NOx sensor in both the first mode and second mode of operation. Specifically, during a SD test, the NOx sensor may first run in the second mode of operation and maintain the $O_2$ concentration in the second cavity 220 to a second level (e.g., 1000 ppm). Then, the NOx sensor may run in the first mode of operation, to obtain measurements and/or estimates for the $O_2$ and $NO_x$ levels. Thus, a completed SD test may be a test in which the NOx sensor has run both in the first mode and second mode of operation. As such, during each completed SD test, NOx and $O_2$ levels may be measured and/or estimated.

In this way, a method may comprise diffusing a portion of exhaust gasses flowing in an exhaust system into a first cavity of a NOx sensor. The method may then comprise applying a first electric potential across a first pumping cell, and pumping oxygen molecules from the first cavity out of the NOx sensor. A portion of the exhaust gasses admitted to the first cavity and not pumped out of the first cavity may then diffuse into a second cavity of the NOx sensor. Additionally, the method may comprise applying a second electric potential across a second pumping cell, and pumping oxygen molecules from the second cavity out of the NOx sensor. In a first mode of operation the concentration of oxygen in the second cavity may be adjusted to a lower first amount. In some examples, the lower first amount may be approximately $10^{-3}$ ppm. In a second mode of operation, the concentration of oxygen in the second cavity may be adjusted to a higher second amount. In some examples, the higher second amount may be approximately 1000 ppm.

The concentration of oxygen in the second cavity may be adjusted by adjusting one or more of the first and second electric potentials applied across the first and second pumping cells, respectively. Thus, in the first mode, the first electric potential applied across the first pumping cell may be greater in the first mode than that applied during the second mode. In other examples, the second electric potential applied across the second pumping cell may be greater in the first mode than that applied during the second mode. In still further examples, the second electric potential applied across both the first and second pumping cells may be greater in the first mode than in the second mode. An oxygen concentration in the exhaust gasses may be estimated based on one or more of a first pumping current resulting from oxygen molecules being pumped out of the first cavity. In some examples, the oxygen concentration may additionally, or alternatively be estimated based on a second pumping current resulting from oxygen molecules being pumped out of the second cavity.

The method may further comprise, applying a third electric potential across a measuring electrode pair. In the first mode the third electric potential may be sufficiently high to dissociate NOx molecules. Thus, in some examples the third electric potential may be 450 mV. Once dissociated, NOx molecules may be pumped out of the second cavity, and a concentration of the NOx may be estimated a third pumping current resulting from oxygen exiting the second cavity. However, in the second mode, the third electric potential may be sufficiently high to dissociate oxygen molecules, and as such, in some examples, in the second mode of operation, the third electric potential may be less than 450 mV. During the second mode of operation, oxygen molecules in the second cavity may be dissociated upon the application of the third electric potential. In some examples, an estimation of the oxygen concentration of the exhaust gasses in the second cavity may be estimated based on the resulting pumping.

Figure 3:
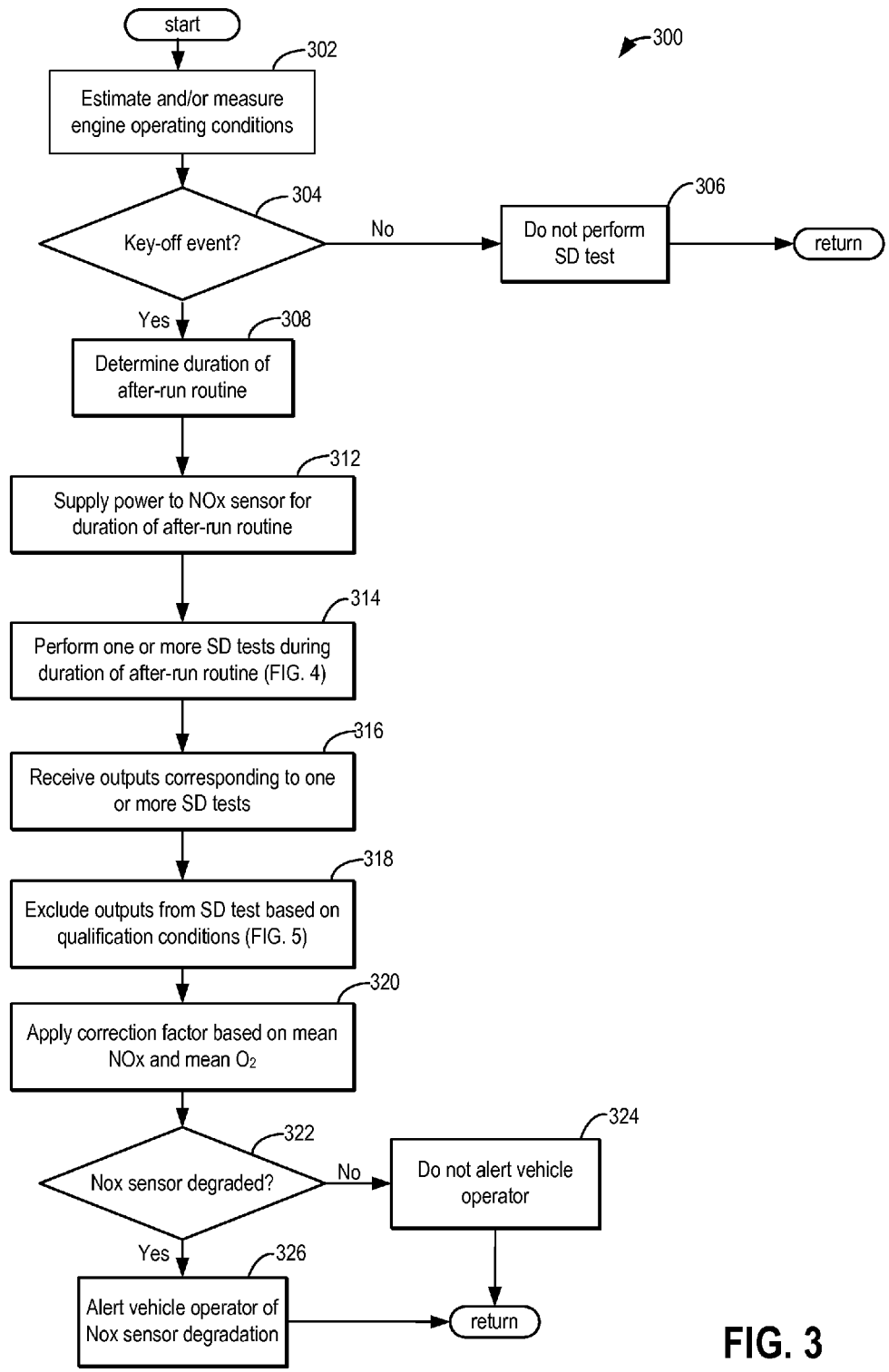
FIG. 3 shows a flow chart of an example method for determining if a NOx sensor is degraded.

Turning now to FIG. 3, it shows an example method 300 for determining if a NOx sensor (e.g. NOx sensor 190, 192 shown in FIG. 1B, NOX sensor 200 shown in FIG. 2) is degraded based on outputs from the sensor during one or more self-diagnostic (SD) tests. As explained above with reference to FIGS. 1-2, the NOx sensor may perform one or more SD tests after a key-off event. However, the concentration of different constituents in the exhaust gas after an engine key-off event may vary. As a result, the outputs of the NOx sensor may be different depending on the exhaust gas properties in an exhaust system (e.g., exhaust system 102 shown in FIG. 1B) at the time an SD test is performed. Outputs from a NOx sensor that is not degraded may vary as much or more between two or more SD tests, than outputs from a NOx sensor that is not degraded and a NOx sensor that is degraded. Therefore, it may be difficult to diagnose and detect NOx sensor that is degraded. The example method 300 shown in FIG. 3 shows a method for determining that a NOx sensor is degraded by excluding SD test results under certain exhaust gas conditions.

Instructions for carrying out method 300 may be executed by a controller (e.g., controller 112 shown in FIG. 1B) based on instructions stored on a memory of the controller and in conjunction with signals received from various sensors of the engine system, such as the sensors described above with reference to FIGS. 1A-1B. Specifically, the controller may execute method 300 based on outputs from the NOx sensor received from a NOx sensor control module (e.g., NOx sensor modules 194 and 198 shown in FIG. 1B). The controller may employ engine actuators of the engine system to adjust engine operation, according to the methods described below.

Method 300 begins at 302, which comprises estimating and/or measuring engine operating conditions. Engine operating conditions may include an exhaust gas temperature, exhaust gas NOx and/or $O_2$ concentration, engine temperature, an intake manifold vacuum, a position of an intake valve, a position of a throttle valve, etc.

After estimating and/or measuring engine operating conditions at 302, method 300 may then continue to 304 and determine if a key-off event has occurred. As described above with reference to FIGS. 1A-1B, an engine key-off event may be where an engine (e.g. engine 110 shown in FIG. 1B) is turned off by a vehicle operator (e.g., vehicle operator 172 shown in FIG. 1B). Thus, the method at 302 may include determining if an input device controlling the operational status of the engine (e.g., ignition in a keyed vehicle, push-button in a keyless vehicle, etc.), has been adjusted to a position signaling the engine to turn off. If it is determined at 304 that a key-off event has not occurred, then the method 300 may proceed to 306, which comprises not performing an SD test. Thus, if a key-off event has not occurred, then the NOx sensor may not perform an SD test. Method 300 then returns.

However, if at 304 it is determined that a key-off event has occurred, then method 300 may proceed to 308, which comprises determining a duration of an after-run routine. An after-run routine may include a duration (e.g., amount of time) for which power to one or more vehicle system components (e.g., NOx sensors 190 and 192 shown in FIG. 1B) may continue to be supplied after the engine is turned. In some examples, the power may be supplied by a glow plug control module (e.g., glow plug control module 156 shown in FIG. 1B). The duration of the after-run routine may be determined based on a desired number of SD tests, and a known duration required to complete one SD test. The duration required to complete one SD test may be stored in the memory of the controller.

Then, method 300 may continue to 312, which comprises supplying power to the NOx sensor for the duration of the after-run routine. In some examples, method 300 may include supplying power to the NOx sensor from the glow plug control module. However, in other examples, method 300 may include supplying power to the NOx sensor from a battery (e.g., battery 184 shown in FIG. 1B). Thus, the controller may send signals to one or more of the glow plug control module and/or the battery to supply power to the NOx sensor for a duration of the after-run routine. However, in other examples, the controller may send signals to the glow plug control module and/or battery to supply power to the NOx sensor for only a portion of the duration of the after-run routine.

Method 300 may then continue from 312 to 314, which comprises performing one or more SD tests during the duration of the after-run routine. The performing of the SD tests may comprise running the NOx sensor in a first mode where a NOx concentration is estimated and/or measured, and in a second mode, where the oxygen concentration in a second chamber (e.g., second cavity 220 shown in FIG. 2) of the NOx sensor is controlled to a higher second level (e.g., 1000 ppm), as described in greater detail in the method shown in FIG. 4. Thus, FIG. 4 may be a subroutine of the method 300 at 314. In some examples, the method 300 at 314 may include the controller sending signals to the NOx control module (e.g., NOx sensor modules 194 and 198 shown in FIG. 1B) for initiating one or more SD tests at the NOx sensor electrically coupled to the control module. Thus at 314, the NOx sensor may receive signals for performing one or more SD tests. In some examples, the controller may send signals to the NOx control module for running one or more SD tests for the entirety of the after-run routine.

After performing the one or more SD results at 314, the method 300 may continue to 316 which comprises receiving outputs (e.g., SD test results data) from the one or more SD tests. Outputs from the SD tests may be received from the NOx sensor control module electrically coupled to the NOx sensor. Further, the outputs may be received by the controller via the CAN bus. The outputs may include measurements and/or estimates of the $O_2$ and/or NOx concentration of the exhaust gas sampled by the NOx sensor during the SD test, tests status, and SD test result. The tests status may be an indication of whether the SD test was completed or cancelled. Further, the SD test result, may be one or more pumping currents output by the NOx sensor during the SD test that is compared to a stored reference value and reported as a percent difference from the stored reference value. In some examples, the SD test result may be a ratio of a pumping current output by a measuring electrode pair (e.g., measuring electrode pair 226, 228 shown in FIG. 2) to a stored value. Since the pumping current output by the measuring electrode pair may be used to estimate the NOx concentration, the SD test result may be a ratio of the estimated NOx concentration to a stored NOx concentration value. Thus, the method at 314, may include comparing a pumping current output by the NOx sensor during the SD test, and comparing that to a value stored in memory of the controller.

After receiving the outputs from the one or more SD tests at 316, method 300 may then proceed to 318 which comprises excluding outputs from the one or more SD tests received at 316 based on qualification conditions. More specifically, the method 300 at 318 may comprises eliminating and/or excluding SD tests results based on the qualification conditions, which is explained in greater detail below with reference to FIGS. 5-6. Thus, the methods described in FIGS. 5-6 may be a subroutine of the method 300 at 318. The qualification conditions may include exhaust gas temperatures, $O_2$ concentrations, NOx concentrations etc. The first completed SD test result generated by the NOx sensor after the key-off event may be excluded at 318. Further, if one or more of the exhaust gas temperature is greater than a threshold, NOx concentration is greater than a threshold, and oxygen concentration is less than a first threshold or greater than a second threshold then that SD test result may be excluded. Said another way, tests results from any SD tests performed where the exhaust gas temperature is greater than a threshold, and/or the oxygen concentration and/or NOx concentration of the exhaust gas is outside a threshold range may be excluded at 318.

It is also important to note that the thresholds for the exhaust gas temperature, $O_2$ concentration, and NOx concentration may also be based on the location of NOx sensor within the exhaust system. For example a NOx sensor (e.g., NOx sensor 190 shown in FIG. 1) positioned upstream of an SCR catalyst (e.g., SCR catalyst 140 shown in FIG. 1) may have different qualification thresholds than a NOx sensor (e.g., NOx sensor 192 shown in FIG. 1) positioned downstream of the SCR catalyst. Said another way, the threshold temperature range, oxygen concentration range, and NOx range used to exclude SD test results may be adjusted depending on the location of the NOx sensor within the exhaust system. However, in other embodiments, the thresholds may be the same for NOx sensor positioned upstream and/or downstream of the SCR catalyst.

After excluding a portion of the SD tests results at 318 method 300 may then proceed to 320, which comprises applying a correction factor to only the SD test results not excluded at 318. The correction factor may be based on the mean NOx and mean $O_2$ measured and/or estimated during the SD test. Additionally, the correction factor may be stored in a look-up table in memory of the controller. Further, the correction factor may be a function of mean $O_2$ and mean NOx measured and/or estimated during the first mode of operation of the NOx sensor in the SD test. Thus, during the portion of the SD test, where the $O_2$ and NOx levels are estimated, the method 300 may include determining the mean of the $O_2$ and NOx concentrations during this portion of the SD test, and then applying a correction factor to the SD test result based on the mean $O_2$ and NOx concentrations. As such, the method 300 at 320 may include modifying the SD test result obtained at 316 based on mean NOx and O₂ levels estimated during the SD test from which the SD test result was received.

It is also important to note that the correction factor may also be based on the location of NOx sensor within the exhaust system. For example a NOx sensor (e.g., NOx sensor 190 shown in FIG. 1) positioned upstream of an SCR catalyst (e.g., SCR catalyst 140 shown in FIG. 1) may have different correction factors than a NOx sensor (e.g., NOx sensor 192 shown in FIG. 1) positioned downstream of the SCR catalyst. However, in other embodiments, the correction factor may be the same for NOx sensor positioned upstream and/or downstream of the SCR catalyst.

Method 300 may then continue from 320 to 322 which comprises determining if the NOx sensor is degraded based on only the SD tests results that were not excluded at 318. Said another way, only SD tests results from completed SD tests after a first completed SD test after an engine key-off event may be used to determine if the NOx sensor is degraded. Further, only SD tests results from completed SD tests where the oxygen concentration measured during the SD test is greater than a first threshold and lower than a second threshold may be used to determine if the NOx sensor is degraded. Additionally, only SD test results from completed SD tests where the temperature of the exhaust gasses measured during the SD test is less than a threshold may be used to determine if the NOx sensor is degraded. In some examples, only SD test results for which the mean NOx concentration measured during the SD tests is less than a threshold may be used to determine if the NOx sensor is degraded in a way that the sensor is skewed low. The method described in FIG. 5, may be executed to determine if the NOx sensor is degraded in a way that the sensor is skewed low. On the other hand, the method described in FIG. 6, may be executed to determine if the NOx sensor is degraded in a way that the sensor is skewed high. Thus, in some examples, where method 300 includes excluding SD tests results based on NOx concentration (e.g., method 500 shown in FIG. 5), method 300 may only be executed to detect a skewed low type of degradation, and not a skewed high type of degradation. However, in other examples, where method 300 does not include excluding SD tests results based on NOx concentration (e.g., method 600 shown in FIG. 6), method 300 may only be executed to detect a skewed high type of degradation, and not a skewed low type of degradation.

In this way, a method may comprise determining if a NOx sensor is degraded based only on outputs from a NOx sensor during an SD test, and only if the outputs are generated from a completed SD test after a first completed SD test after an engine key-off event, where the estimated and/or measured temperature of exhaust gasses sampled by the NOx sensor and/or flowing past the NOx sensor during the SD test is below a threshold, the estimated and/or measured oxygen concentration of exhaust gasses sampled by the NOx sensor during the SD test is above a first threshold and below a second threshold.

Additionally in some examples, determining if the NOx sensor is degraded may be based only on outputs from a NOx sensor during an SD test, and only if the outputs are generated from a completed SD test after a first completed SD test after an engine key-off event, where the estimated and/or measured temperature of exhaust gasses sampled by the NOx sensor and/or flowing past the NOx sensor during the SD test is below a threshold, the estimated and/or measured oxygen concentration of exhaust gasses sampled by the NOx sensor during the SD test is above a first threshold and below a second threshold, and where the estimated and/or measured NOx concentration of exhaust gasses sampled by the NOx sensor during the SD test is below a threshold. Put more simply, NOx concentrations of exhaust gasses sampled by the NOx sensor during the SD test may in some examples be used to disqualify SD test results. However, in other examples, such as when determining if the NOx sensor is degraded in a skewed low manner, the SD test results may be used to determine if the NOx sensor is degraded regardless of outputs generated by the NOx sensor during a portion of the SD test corresponding to NOx concentrations.

Determining if the NOx sensor is degraded at 322 may include comparing the SD test result to a lower first threshold, and a higher second threshold. If the SD test result is less than the lower first threshold or higher than the higher second threshold, then it may be determined at 322 that the NOx sensor is degraded. The lower first threshold and higher second threshold may in some example be pre-set values stored in the memory of the controller. Thus, in some examples, the first threshold and second threshold may be constant. However, in other examples, the first threshold and second threshold may be based as a function of mean NOx concentration. As such, the first threshold and second thresholds may monotonically increase with increasing mean NOx concentrations, where the mean NOx concentrations are estimated based on the outputs received at 316. Specifically, the mean NOx concentrations received at 316 may be NOx concentrations estimated over a duration, where the duration is a portion and/or all of the duration of the SD test. As such, the mean NOx concentration may be calculated based on a plurality outputs corresponding to a plurality of NOx concentrations, taken over a portion of the duration of the SD test. Further the threshold may also be based on the location of the NOx sensor in the exhaust system. For example the threshold may be different for a NOx sensor positioned downstream of the SCR catalyst than for a NOx sensor positioned upstream of the SCR catalyst.

However, in other examples, determining if the NOx sensor is degraded at 322 may include comparing the SD test result to a stored reference value. As described above the stored reference value may be a function, and may be based on mean NOx concentration. In some examples, where the value is a function, the function may monotonically increase with increasing mean NOx concentration. However, it may be determined that the NOx sensor is degraded if the difference from the SD test result and the stored reference value is greater than a threshold. Said another way, the method may comprise determining that the NOx sensor is degraded if the SD test result is different from the stored reference value by more than a threshold amount.

If it is determined that the NOx SD test result is less than the first threshold or greater than the second threshold at 322, then it may be determined that the NOx sensor is degraded, and method 300 continues to 326 which may comprise alerting the vehicle operator of the NOx sensor degradation. In some examples, the alerting the vehicle operator may include generating a warning light or indicator via a light, LED display, touch screen display, etc., on a vehicle display and/or dashboard of a vehicle. Method 300 then returns.

However, if it is determined that the SD test result is in-between the first and second thresholds, then it may be determined that the NOx sensor is not degraded, and method 300 may proceed from 322 to 324, which comprises not alerting the vehicle operator. Method 300 then returns.

In this way, a method may comprise after a vehicle ignition key-off event: running multiple nitrogen oxide (NOx) sensor self-diagnostic tests, where running each test comprises running the NOx sensor in a first mode and a second mode. Thus a SD test may only be rendered complete, if the NOx sensor has been run in both the first mode and the second mode. In the first mode, the method may comprise applying a first electric potential across an electrode pair of a nitrogen oxide (NOx) sensor so that an oxygen concentration in an internal cavity of the NOx sensor may be adjusted to a lower first level, and generating a first output where the first output is indicative of a NOx concentration. The second mode may comprise applying a second electric potential across the electrode pair so that an oxygen concentration in an internal cavity of the NOx sensor may be adjusted to a higher second level, and generating a second output. In some examples the second output may be indicative of an oxygen concentration in the internal cavity.

The method may additionally or alternatively comprise estimating a temperature of exhaust gasses being sampled and/or flowing past the NOx sensor based on outputs from a temperature sensor. In some examples, the temperature sensor may be aligned with the NOx sensor relative to a flow of exhaust gasses.

As such, the temperature, oxygen concentration, and NOx concentration of exhaust gasses being sampled and/or flowing past the NOx sensor during a portion and/or all of a duration of each SD test may be estimated. The temperature, oxygen concentration, and NOx concentration may be transmitted to a controller via a CAN bus, along with an indication of whether each SD test was completed or cancelled. Further, the order in which the SD tests occurred after the key-off event may be transmitted to the controller.

The method may further comprise calculating a mean for the oxygen concentration, NOx concentration, and temperature for each SD test. Additionally or alternatively, the method may comprise determining that the sensor is degraded if the first output is different from a reference value by more than a threshold, only if the oxygen concentration is greater than a first threshold and less than a second threshold, the temperature is less than a threshold, and the SD test was completed after a first completed SD test following the key-off event. Additionally, the method may comprise determining that the sensor is degraded if the first output is different from a reference value by more than a threshold, only if the NOx concentration is less than threshold.

Turning now to FIG. 4, it shows an example method 400 for performing a NOx sensor SD test. Thus, method 400 may be executed at 314 in method 300 shown above with reference to FIG. 3. As such, method 400 may be executed in conjunction with method 300 shown in FIG. 3. The example method 400 shows how operation of a NOx sensor (e.g., NOx sensor 190, 192 shown in FIG. 1B, NOX sensor 200 shown in FIG. 2) may be adjusted during a SD test. During an SD test, the NOx sensor may operate in two modes, a first mode and a second mode. In some examples, the NOx sensor may perform the second mode before performing the first mode.

As described above with reference to FIG. 2, the NOx sensor may admit a portion of exhaust gasses flowing in an exhaust system (e.g., exhaust system 102 shown in FIG. 1B) to a first chamber (e.g., first cavity 212 shown in FIG. 2). Exhaust gasses may then diffuse into a second chamber (e.g., second cavity 220 shown in FIG. 2). Oxygen may be pumped out of the first chamber and second chamber by a first pumping cell (e.g., first pumping electrode pair 214, 216 shown in FIG. 2) and second pumping cell (e.g., second pumping electrode pair 222, 216 shown in FIG. 2), respectively. In the first mode of operation, the oxygen concentration in the second chamber may be adjusted to a first level (e.g., $10^{-3}$ ppm). As such, in the first mode, oxygen may be effectively removed from the second chamber, and then an electric potential sufficient to dissociate NOx molecules may be applied to a measuring electrode pair (e.g., measuring electrode pair 226, 228 shown in FIG. 2) in the second chamber to measure an amount of NOx in the sampled exhaust gasses. An amount of oxygen in the exhaust gasses may be estimated based on a pumping current measured at the first pumping cell. Thus, the NOx sensor may be run in the first mode during normal engine operation when an engine (e.g., engine 110 shown in FIG. 1B) is on (e.g., not after an engine key-off event). As such, the NOx sensor may be run in the first mode to measure an amount of NOx and/or oxygen in exhaust gasses flowing through the exhaust system.

However, during an SD test, the NOx sensor may be operated in the first mode and a second mode, where in the second mode, the concentration of oxygen in the second chamber may be maintained at a higher second level (e.g., 1000 ppm). Thus, during the second mode of operation the electric potential applied to a measuring electrode pair may dissociate the oxygen molecules in the second chamber, and thus the concentration of oxygen in the second chamber may be measured. Thus, in the second mode of operation, the oxygen concentration in the second chamber may be measured.

Instructions for carrying out method 400 may be executed by a control module (e.g., NOx sensor modules 194, 198 shown in FIG. 1B) based on instructions stored on a memory of the control module and in conjunction with signals received from a NOx sensor (e.g., NOx sensors 190 and 192 shown in FIG. 1B) and a controller (e.g., controller 112 shown in FIG. 1B) via a CAN bus (e.g., CAN bus 152 shown in FIG. 1B). The controller may employ engine actuators of the engine system to adjust engine operation, according to the methods described below. Thus, the NOx sensor module may adjust electric voltage applied to the NOx sensor based on signals received from the controller. Specifically, the controller may send a signal to the NOx control module to run one or more SD tests via the CAN bus. The NOx control module may perform the SD test, and report outputs from the NOx sensor back to the controller via the CAN bus. Specifically, the outputs may include signals corresponding to the status of the SD test (e.g., active, complete, incomplete, cancelled, etc.), an SD test result, NOx concentrations, and oxygen concentrations.

Said another way, one or more of the status of the SD test, a SD test result, NOx concentrations, and oxygen concentrations may be estimated based on outputs from the NOx sensor. As described below, the SD test result, NOx concentrations, and oxygen concentrations may be estimated only based on outputs from the NOx sensor during a portion of the SD test. Specifically, the SD test result, NOx concentrations, and oxygen concentrations may only be estimated based on outputs from the NOx sensor during a first mode of the SD test, where a concentration of oxygen in a cavity of the NOx sensor is adjusted to a lower first level (e.g., $10^{-3}$ ppm). The NOx concentrations may be an estimated concentration of NOx in exhaust gasses sampled by the NOx sensor. Similarly, the oxygen concentrations may be an estimated concentration of oxygen in exhaust gasses sampled by the NOx sensor. The outputs transmitted to the controller from the NOx sensor and/or control module may then be used by the controller to perform a method, such as the method 300 described above with reference to FIG. 3.

Method 400 begins at 402, which comprises estimating and/or measuring exhaust system operating conditions. Exhaust system operating conditions may include an exhaust gas temperature, exhaust gas NOx and/or $O_2$ concentration, etc.

After estimating exhaust system operating parameters, method 400 may continue to 404 which comprises determining if an SD test is desired. An SD test may be desired after an engine key-off event. Thus, the method 400 may additionally comprise determining if an engine key-off event has occurred in a manner similar that at 304 of method 300 described above with reference to FIG. 3. If an engine key-off event has not occurred and/or an SD test is not desired, method 400 may proceed to 406 which comprises not performing an SD test. Thus, at 406, an SD test may not be performed at the NOx sensor. Method 400 then returns. However, if at 404 it is determined that an engine key-off event has occurred and an SD test is desired, then method 400 continues to 408 and runs the NOx sensor in a second mode to control the oxygen concentration in the second chamber to a higher second threshold.

In the second mode of operation, a second electric potential (VIp1 shown in FIG. 2) applied across the second pumping cell may be adjusted to a second level to maintain the oxygen concentration in the second chamber at approximately a higher second threshold. In some examples the second threshold may be approximately 1000 ppm of oxygen. In some examples, the second mode of operation may additionally include applying a third electric potential across the measuring electrode pair and estimating an oxygen concentration in the second chamber based on the resulting pumping current.

After running the NOx sensor in the second mode, method 400 may then continue to 410, and run the NOx sensor in a first mode to control the oxygen concentration in the second chamber to a lower first threshold and measure NOx and oxygen levels (e.g., concentrations). In the first mode, a first electric potential (VIp0 shown in FIG. 2) applied across the first pumping cell, and the second electric potential applied across the second pumping cell may be adjusted to remove oxygen from the exhaust gas in the first chamber, and thereby reduce the concentration of oxygen in the second chamber to a lower first level. In some examples the first level may be approximately $10^{-3}$ ppm of oxygen. The oxygen concentration of the exhaust gas may also be estimated based on the resulting pumping current (e.g., Ip0 shown in FIG. 2) from the first electric potential applied across the first pumping cell. Further, the first mode of operation may additionally include adjusting the third electric potential applied across the measuring electrode pair to a level high enough to dissociate NOx molecules (e.g., 450 mV), and estimating the NOx concentration based on the resulting pumping current.

Thus, the method at 410 may include measuring and/or estimating NOx and/or oxygen levels in the exhaust gas based on outputs of the NOx sensor during an SD test. More specifically, the NOx and/or oxygen concentrations may be estimated based on outputs from the NOx sensor during the first mode of operation of the NOx sensor during the SD test. As such, NOx and/or oxygen concentrations may be estimated for a duration, where the duration may be a portion of the duration of an SD test. Said another way, a completed SD test may last a duration (e.g., 17 seconds). NOx and/or oxygen concentrations may be estimated over a portion of the duration of the SD test. Specifically the oxygen levels may be based on a first pumping current (e.g., Ip0 shown in FIG. 2) and/or a second pumping current (e.g., Ip1 shown in FIG. 2) during a first mode of NOx sensor operation. Additionally, during the first mode of operation, the NOx level may be estimated based on a third pumping current (e.g., Ip2 shown in FIG. 2). Further, during the first mode of operation at 410, an SD test result may be generated. The SD test result may be generated based on one or more of the first, second, and third pumping currents. In some examples, the SD test result may be based on only the third pumping current. However, in other examples, the SD test result may be based on the first pumping current, second pumping current, and third pumping current. In still further examples, the SD test result may be based on the second and third pumping currents.

Method 400 may then continue from 410 to 412 which comprises comparing the SD test result to a stored value. Thus, the one or more pumping currents corresponding to the SD test result at 410, may be compared to a reference value stored in the memory of the controller. The comparing may include dividing the SD test result by the stored reference value, and reporting the SD test result as a percentage of the stored reference value. Thus, if the SD test result is the same as the stored reference value, then the SD test result may be reported at 412 as 100%. If the SD test result is greater than the stored reference value, then the SD test result may be reported as a percentage greater than 100%. Further, if the SD test result is less than the stored reference value, then the SD test result may be reported as a percentage less than 100%. However, in other examples, the SD test result may be reported as a ratio. Thus, if the SD test result is the same as the stored reference value, then the SD test result may be reported at 412 as 1. If the SD test result is greater than the stored reference value, then the SD test result may be reported as decimal value greater than 1. If the SD test result is less than the stored reference value, then the SD test result may be reported as a decimal value smaller than 1.

The reference value may be different depending on the positioning of the NOx sensor within an exhaust system (e.g., exhaust system 102 shown in FIG. 1B). For example, the reference value may be different for a first NOx sensor (e.g., NOx sensor 190 shown in FIG. 1B) positioned upstream of an SCR catalyst (e.g., SCR catalyst 140 shown in FIG. 1B), than for a second NOx sensor (e.g., NOx sensor 192 shown in FIG. 1B) positioned downstream of the SCR catalyst.

The method 400 may then proceed from 412 to 414, which comprises transmitting the oxygen and NOx levels (e.g. concentrations) measured and/or estimated at 410 and/or the SD test result reported at 410. In some examples, the method 400 at 414 may include transmitting the oxygen and NOx level measured and/or estimated at 410 and/or the SD test result reported at 410 to the controller. Thus, at 414, the NOx control module may transmit the SD test result, oxygen concentration, and NOx concentration, measured and/or estimated over the duration of the SD test performed at 408-412 to the controller via the CAN bus. Method 400 then returns.

Turning now to FIG. 5, it shows an example method 500 for excluding SD tests results received from a NOx sensor (e.g. NOx sensor 190, 192 shown in FIG. 1B, NOX sensor 200 shown in FIG. 2) based on a set of qualifying conditions. Method 500 may be executed as part of a method (e.g., method 300 shown in FIG. 3) for determining if the NOx sensor is degraded in a way that is skewed low. Thus, a method such as the method 500 may be executed as a subroutine of method 300 at 318. Said another way, method 500 may be executed as part of a method, such as the method 300 shown in FIG. 3, to determine if a NOx is degraded in a way that is skewed low. As explained above with reference to FIG. 1, the NOx sensor may perform one or more SD tests after a key-off event. Results from the NOx sensor may first be transmitted to a NOx sensor control module (e.g., NOx sensor modules 194 and 198 shown in FIG. 1B), before being relayed to a controller (e.g., controller 112) via a CAN bus (e.g., CAN bus 152 shown in FIG. 1B). Specifically, the NOx sensor control module may send a status of the SD test (e.g., complete, cancelled, active, etc.), an SD test result, oxygen concentration, and NOx concentration to the controller. The controller may then exclude SD tests results based on the set of qualifying conditions. A method such as the method 500 shown in FIG. 5, may be performed by the controller to exclude SD tests results based on the qualification conditions.

Instructions for carrying out method 500 may be executed by a controller (e.g., controller 112 shown in FIG. 1B) based on instructions stored on a memory of the controller and in conjunction with signals received from various sensors of the engine system, such as the sensors described above with reference to FIGS. 1A-1B. Specifically, the controller may execute method 500 based on outputs from the NOx sensor received from the NOx sensor control module. The controller may employ engine actuators of the engine system to adjust engine operation, according to the methods described below.

Method 500 begins at 502, which comprises estimating and/or measuring engine operating conditions. Engine operating conditions may include an exhaust gas temperature, exhaust gas NOx and/or $O_2$ concentration, engine temperature, an intake manifold vacuum, a position of an intake valve, a position of a throttle valve, etc.

After estimating and/or measuring engine operating conditions, method 500 may proceed to 504 which comprises receiving outputs from an SD test. The outputs received from the SD test may include one or more of an SD test status, oxygen concentrations, NOx concentrations, and SD test result. As described above with reference to FIGS. 3 and 4, the test status may be generated by the NOx sensor control module and may indicate whether the SD test is complete or incomplete. Further, the oxygen concentrations of the exhaust gas as estimated and/or measured by the NOx sensor during the SD test may be received at 504. Additionally, the NOx concentration of the exhaust gas as estimated and/or measured by the NOx sensor during the SD test may be received at 504. Specifically, as described above with reference to FIG. 4, the oxygen concentration and NOx concentration may be estimated and/or measured during the first mode of operation of the NOx sensor during the SD test. The SD test result may be reported as a percentage value compared to a stored value in the NOx sensor control module as described above with reference to FIG. 4.

After receiving the outputs from the SD test at 504, method 500 may proceed to 505, 506, 510, 512, and/or 514 in any order. In some examples, 505-514 may be executed simultaneously. However, in the example shown in FIG. 5, method 500 may proceed from 504 to 505 which comprises determining if the SD test is completed. Said another way, the method 500 at 505 may comprise determining if the output (e.g., SD test result) received at 504 is from a completed SD test. The NOx sensor control module may send a signal to the controller indicating whether the SD test has been completed, or cancelled. Thus, determining whether or not the SD test is complete may be based on signals received from the NOx sensor control module.

If the SD test from which the outputs were received at 504, is determined at 505 to not be complete, then method 500 may proceed to 508, which comprises excluding the outputs from the SD test. More specifically, the method 500 at 508 may comprise excluding the SD test result from the SD test. Thus, if the SD is not completed, then the outputs received from the NOx sensor for that SD test may be excluded. As described above with reference to FIG. 3, SD tests results and/or outputs received from the NOx sensor that are excluded at 508 may not be used in determining whether or not the NOx sensor is degraded such as at 322 in method 300 in FIG. 3. Thus, the method at 508 comprises excluding SD test results and/or outputs received from the NOx sensor for SD tests that have not been completed. More simply, if the SD test does not have a completed status signal, then the SD test results for that SD test may be excluded, and may not be used to determine if the NOx sensor is degraded.

However, if it is determined that the SD test is complete at 505, then method 500 may proceed to 506 which comprises determining if the mean temperature of exhaust gasses sampled by the NOx sensor and/or flowing past the NOx sensor during the SD test is less than a threshold. The threshold may be stored in memory of the controller. Further the threshold may be a temperature above which, urea may be converted to $NH_3$ at more than a threshold rate. Thus, the threshold temperature may represent a temperature above, which $NH_3$ may be registered as NOx by the NOx sensor.

In some examples the mean temperature may only be the mean temperature of exhaust gasses during the first mode of operation of the NOx sensor during the SD test. The temperature of exhaust gasses may be estimated based on outputs from a temperature sensor (e.g., temperature sensor 191, 193 shown in FIG. 1B), aligned with the NOx sensor in an exhaust system (e.g., exhaust system 102 shown in FIG. 1B). Thus, as described above with reference to FIG. 1B, the temperature sensor may be superposed with respect to the NOx sensor and thus may be configured to measure the temperature of exhaust gasses flowing past and/or being sampled at the NOx sensor.

If the mean temperature of the exhaust gasses being sampled at the NOx sensor and/or flowing past the sensor during the SD test is not less than the threshold at 506, then method 500 proceeds to 508 which comprises excluding outputs received from the NOx sensor for that SD test. Thus, if the mean exhaust gas temperature of exhaust gasses being sampled at the NOx sensor during all or a portion of the SD test exceeds the threshold, then the SD test result and/or outputs received from the NOx sensor for that SD test may be excluded. As described above with reference to FIG. 3, SD tests results and/or outputs received from the NOX sensor that are excluded at 508 may not be used in determining whether or not the NOx sensor is degraded such as at 322 in method 300 in FIG. 3. Thus, the method at 508 comprises excluding outputs received from the NOx sensor from SD tests where the estimated and/or measured temperature of exhaust gasses sampled by the NOx sensor and/or flowing past the NOx sensor during the SD test is above a threshold. More simply, if the exhaust gas temperature as estimated and/or measured based on outputs of the temperature sensor arranged in line with the NOx sensor relative to the flow of exhaust gasses during an SD test is greater than a threshold, then the SD test results for that SD test may be excluded, and may not be used to determine if the NOx sensor is degraded.

Returning to 506, if it is determined that the mean temperature of exhaust gasses is less than the threshold at 506, then method 500 may continue to 510, which comprises determining if the oxygen concentration of exhaust gasses estimated and/or measured during the first mode of operation of the SD test, is greater than a lower first threshold and less than a higher second threshold. The first and second threshold may be stored in the memory of the controller. As described above with reference to FIG. 4, the oxygen concentration may be estimated based on one or more of a first pumping current (e.g., Ip0) and second pumping current (e.g., Ip1) from a first pumping cell (e.g., first pumping electrode pair 214, 216 shown in FIG. 2) and second pumping cell (e.g., second pumping electrode pair 222, 216 shown in FIG. 2), respectively. Further, as described above with reference to FIG. 4, the oxygen concentration may be estimated during a first mode of operation of the NOx sensor during the SD test, where the oxygen concentration in a second chamber (e.g., second internal cavity 220 shown in FIG. 2) of the NOx sensor is reduced from that of a first chamber (e.g., first internal cavity 212 shown in FIG. 2) to a lower first level (e.g., $10^{-3}$ ppm). If the oxygen concentration is less than the first threshold, or greater than the second threshold, then method 500 may continue to 508 and exclude the outputs from the SD test.

Thus, the method at 508 comprises excluding outputs (e.g., SD test results) from SD tests where the estimated and/or measured oxygen concentration of exhaust gasses sampled by the NOx sensor during the SD test is below a first threshold or above a second threshold. More simply, if the oxygen concentration as estimated and/or measured based on outputs of the NOx sensor during an SD test is less than a first threshold or greater than a second threshold, then the outputs and/or SD test results received from the NOx sensor for that SD test may be excluded, and may not be used to determine if the NOx sensor is degraded.

However, if the oxygen concentration is between the first and second threshold at 510, then method 500 may continue to 512, which comprises determining if the outputs (e.g., SD test results) received from the NOx sensor are from a first completed SD test after an engine key-off event. As described above with reference to FIG. 3, multiple SD tests may be performed after an engine key-off event. However, the method 500 at 510 may include determining if the outputs received from the NOx sensor are from the first SD test completed after an engine key-off event, so that results from the first completed SD test after the engine key-off event may be excluded.

If it is determined at 512, that the outputs (e.g., SD test results) are from the first SD test completed after an engine key-off event, then method 500 may continue to 508 and exclude the outputs (e.g., SD test results). Thus, the method 500 at 508 may comprise only including the second and subsequent SD tests completed after an engine key-off event, and not including the first SD test completed after an engine key-off event. For example, if after an engine key-off event, the NOx sensor first completes a first SD test, and then completes a second SD test before power to the NOx sensor ceases, or the controller stops sending signals to the NOx sensor control module to perform additional SD tests, then only outputs from the NOx sensor during the second SD test may be used to determine if the NOx sensor is degraded. However, if at 512 it is determined that the outputs (e.g., SD test results) are not from the first completed SD test after an engine key-off event, then method 500 may continue to 514 which comprises determining if the NOx concentration is less than a threshold.

As described above with reference to FIG. 4, the NOx concentration may be estimated based on outputs from the NOx sensor during the first mode of operation during an SD test. Specifically, the NOx concentration may be estimated based on a pumping current (e.g., Ip2 shown in FIG. 2) from a measuring electrode pair (e.g., measuring electrode pair 226, 228 shown in FIG. 2). The threshold may be a NOx level (e.g., concentration) stored in the memory of the controller. If it is determined at 514 that the NOx concentration is not less than the threshold, method 500 continues to 508 which comprises excluding the outputs from the NOx sensor during that SD test. Thus, the method at 508 comprises excluding SD test results from SD tests where the estimated and/or measured NOx concentration of exhaust gasses sampled by the NOx sensor during the SD test is above a threshold. More simply, if the NOx concentration as estimated and/or measured based on outputs of the NOx sensor during an SD test is greater than a threshold, then the SD test results for that SD test may be excluded, and may not be used to determine if the NOx sensor is degraded.

However, if at 514 it is determined that the NOx concentration is less than the threshold at 514, then method 500 continues to 516 which comprises not excluding the SD test result, and using the SD test result to determine if the NOx sensor is degraded, such as in the manner described above with reference to 322 of method 300 in FIG. 3. Method 500 then returns.

Thus, the method 500 at 508 comprises excluding SD test results from SD tests where the estimated and/or measured temperature of exhaust gasses sampled by the NOx sensor and/or flowing past the NOx sensor during the SD test is above a threshold, SD test results from SD tests where the estimated and/or measured oxygen concentration of exhaust gasses sampled by the NOx sensor during the SD test is below a first threshold or above a second threshold, SD test results from the first SD test completed after an engine key-off event, and SD test results from SD tests where the estimated and/or measured NOx concentration of exhaust gasses sampled by the NOx sensor during the SD test is above a threshold.

As such, the method 500 at 516 comprises only including SD tests results from SD tests where the estimated and/or measured temperature of exhaust gasses sampled by the NOx sensor and/or flowing past the NOx sensor during the SD test is below a threshold, SD test results from SD tests where the estimated and/or measured oxygen concentration of exhaust gasses sampled by the NOx sensor during the SD test is above a first threshold and below a second threshold, SD test results from the first SD test completed after a first completed SD test after an engine key-off event, and SD test results from SD tests where the estimated and/or measured NOx concentration of exhaust gasses sampled by the NOx sensor during the SD test is below a threshold.

Turning now to FIG. 6, it shows an example method 600 for excluding SD tests results received from a NOx sensor (e.g. NOx sensor 190, 192 shown in FIG. 1B, NOX sensor 200 shown in FIG. 2) based on a set of qualifying conditions. Method 600 may be executed as part of a method (e.g., method 300 shown in FIG. 3) for determining if the NOx sensor is degraded in a way that is skewed high. Thus, a method such as the method 600 may be executed as a subroutine of method 300 at 318. Said another way, method 600 may be executed as part of a method, such as the method 300 shown in FIG. 3, to determine if a NOx is degraded in a way that is skewed high.

While FIG. 5 shows a method for determining if the NOx sensor is degraded in a way that is skewed low, the method 600 described in FIG. 6 may be executed to determine if the NOx sensor is degraded in a way that is skewed high. Thus, the methods described in FIGS. 5-6 may in some examples, both be executed, to determine if the NOx sensor is degraded in a way that is skewed low or skewed high. While the method in FIG. 5 includes excluding SD tests results received from the NOx sensor if the NOx concentrations as estimated from outputs of the NOx sensor during the SD test are below a threshold, the method 600 described in FIG. 6 does not include excluding SD tests results based on the NOx concentrations of exhaust gasses sampled at the NOx sensor during an SD test.

As explained above with reference to FIG. 1, the NOx sensor may perform one or more SD tests after a key-off event. Results from the NOx sensor may first be transmitted to a NOx sensor control module (e.g., NOx sensor modules 194 and 198 shown in FIG. 1B), before being relayed to a controller (e.g., controller 112) via a CAN bus (e.g., CAN bus 152 shown in FIG. 1B). Specifically, the NOx sensor control module may send a status of the SD test (e.g., complete, cancelled, active, etc.), an SD test result, oxygen concentration, and NOx concentration to the controller. The controller may then exclude SD tests results based on the set of qualifying conditions. A method such as the method 600 shown in FIG. 6, may be performed by the controller to exclude SD tests results based on the qualification conditions.

Instructions for carrying out method 600 may be executed by a controller (e.g., controller 112 shown in FIG. 1B) based on instructions stored on a memory of the controller and in conjunction with signals received from various sensors of the engine system, such as the sensors described above with reference to FIGS. 1A-1B. Specifically, the controller may execute method 600 based on outputs from the NOx sensor received from the NOx sensor control module. The controller may employ engine actuators of the engine system to adjust engine operation, according to the methods described below.

Method 600 begins at 602, which comprises estimating and/or measuring engine operating conditions. Engine operating conditions may include an exhaust gas temperature, exhaust gas NOx and/or $O_2$ concentration, engine temperature, an intake manifold vacuum, a position of an intake valve, a position of a throttle valve, etc.

After estimating and/or measuring engine operating conditions, method 600 may proceed to 604 which comprises receiving outputs from an SD test. The outputs received from the SD test may include one or more of an SD test status, oxygen concentrations, NOx concentrations, and SD test result. As described above with reference to FIGS. 3 and 4, the test status may be generated by the NOx sensor control module and may indicate whether the SD test is complete or incomplete. Further, the oxygen concentrations of the exhaust gas as estimated and/or measured by the NOx sensor during the SD test may be received at 604. Additionally, the NOx concentration of the exhaust gas as estimated and/or measured by the NOx sensor during the SD test may be received at 604. Specifically, as described above with reference to FIG. 4, the oxygen concentration and NOx concentration may be estimated and/or measured during the first mode of operation of the NOx sensor during the SD test. The SD test result may be reported as a percentage value compared to a stored value in the NOx sensor control module as described above with reference to FIG. 4.

After receiving the outputs from the SD test at 604, method 600 may proceed to 605, 606, 610, and/or 612, in any order. In some examples, 605-612 may be executed simultaneously. However, in the example shown in FIG. 6, method 600 may proceed from 604 to 605 which comprises determining if the SD test is completed. Said another way, the method 600 at 605 may comprise determining if the output (e.g., SD test result) received at 604 is from a completed SD test. The NOx sensor control module may send a signal to the controller indicating whether the SD test has been completed, or cancelled. Thus, determining whether or not the SD test is complete may be based on signals received from the NOx sensor control module.

If the SD test from which the outputs were received at 604, is determined at 605 to not be complete, then method 600 may proceed to 608, which comprises excluding the outputs from the SD test. More specifically, the method 600 at 608 may comprise excluding the SD test result from the SD test. Thus, if the SD is not completed, then the outputs received from the NOx sensor for that SD test may be excluded. As described above with reference to FIG. 3, SD tests results and/or outputs received from the NOx sensor that are excluded at 608 may not be used in determining whether or not the NOx sensor is degraded such as at 322 in method 300 in FIG. 3. Thus, the method at 608 comprises excluding SD test results and/or outputs received from the NOx sensor for SD tests that have not been completed. More simply, if the SD test does not have a completed status signal, then the SD test results for that SD test may be excluded, and may not be used to determine if the NOx sensor is degraded.

However, if it is determined that the SD test is complete at 605, then method 600 may proceed to 606 which comprises determining if the mean temperature of exhaust gasses sampled by the NOx sensor and/or flowing past the NOx sensor during the SD test is less than a threshold. The threshold may be stored in memory of the controller. Further the threshold may be a temperature above which, urea may be converted to $NH_3$ at more than a threshold rate. Thus, the threshold temperature may represent a temperature above, which $NH_3$ may be registered as NOx by the NOx sensor.

In some examples the mean temperature may only be the mean temperature of exhaust gasses during the first mode of operation of the NOx sensor during the SD test. The temperature of exhaust gasses may be estimated based on outputs from a temperature sensor (e.g., temperature sensor 191, 193 shown in FIG. 1B), aligned with the NOx sensor in an exhaust system (e.g., exhaust system 102 shown in FIG. 1B). Thus, as described above with reference to FIG. 1B, the temperature sensor may be superposed with respect to the NOx sensor and thus may be configured to measure the temperature of exhaust gasses flowing past and/or being sampled at the NOx sensor.

If the mean temperature of the exhaust gasses being sampled at the NOx sensor and/or flowing past the sensor during the SD test is not less than the threshold at 606, then method 600 proceeds to 608 which comprises excluding outputs received from the NOx sensor for that SD test. Thus, if the mean exhaust gas temperature of exhaust gasses being sampled at the NOx sensor during all or a portion of the SD test exceeds the threshold, then the SD test result and/or outputs received from the NOx sensor for that SD test may be excluded. As described above with reference to FIG. 3, SD tests results and/or outputs received from the NOX sensor that are excluded at 608 may not be used in determining whether or not the NOx sensor is degraded such as at 322 in method 300 in FIG. 3. Thus, the method at 608 comprises excluding outputs received from the NOx sensor from SD tests where the estimated and/or measured temperature of exhaust gasses sampled by the NOx sensor and/or flowing past the NOx sensor during the SD test is above a threshold. More simply, if the exhaust gas temperature as estimated and/or measured based on outputs of the temperature sensor arranged in line with the NOx sensor relative to the flow of exhaust gasses during an SD test is greater than a threshold, then the SD test results for that SD test may be excluded, and may not be used to determine if the NOx sensor is degraded.

Returning to 606, if it is determined that the mean temperature of exhaust gasses is less than the threshold at 606, then method 600 may continue to 610, which comprises determining if the oxygen concentration of exhaust gasses estimated and/or measured during the first mode of operation of the SD test, is greater than a lower first threshold and less than a higher second threshold. The first and second threshold may be stored in the memory of the controller. As described above with reference to FIG. 4, the oxygen concentration may be estimated based on one or more of a first pumping current (e.g., Ip0) and second pumping current (e.g., Ip1) from a first pumping cell (e.g., first pumping electrode pair 214, 216 shown in FIG. 2) and second pumping cell (e.g., second pumping electrode pair 222, 216 shown in FIG. 2), respectively. Further, as described above with reference to FIG. 4, the oxygen concentration may be estimated during a first mode of operation of the NOx sensor during the SD test, where the oxygen concentration in a second chamber (e.g., second internal cavity 220 shown in FIG. 2) of the NOx sensor is reduced from that of a first chamber (e.g., first internal cavity 212 shown in FIG. 2) to a lower first level (e.g., $10^{-3}$ ppm). If the oxygen concentration is less than the first threshold, or greater than the second threshold, then method 600 may continue to 608 and exclude the outputs from the SD test.

Thus, the method at 608 comprises excluding outputs (e.g., SD test results) from SD tests where the estimated and/or measured oxygen concentration of exhaust gasses sampled by the NOx sensor during the SD test is below a first threshold or above a second threshold. More simply, if the oxygen concentration as estimated and/or measured based on outputs of the NOx sensor during an SD test is less than a first threshold or greater than a second threshold, then the outputs and/or SD test results received from the NOx sensor for that SD test may be excluded, and may not be used to determine if the NOx sensor is degraded.

However, if the oxygen concentration is between the first and second threshold at 610, then method 600 may continue to 612, which comprises determining if the outputs (e.g., SD test results) received from the NOx sensor are from a first completed SD test after an engine key-off event. As described above with reference to FIG. 3, multiple SD tests may be performed after an engine key-off event. However, the method 600 at 610 may include determining if the outputs received from the NOx sensor are from the first SD test completed after an engine key-off event, so that results from the first completed SD test after the engine key-off event may be excluded.

If it is determined at 612, that the outputs (e.g., SD test results) are from the first SD test completed after an engine key-off event, then method 600 may continue to 608 and exclude the outputs (e.g., SD test results). Thus, the method 600 at 608 may comprise only including the second and subsequent SD tests completed after an engine key-off event, and not including the first SD test completed after an engine key-off event. For example, if after an engine key-off event, the NOx sensor first completes a first SD test, and then completes a second SD test before power to the NOx sensor ceases, or the controller stops sending signals to the NOx sensor control module to perform additional SD tests, then only outputs from the NOx sensor during the second SD test may be used to determine if the NOx sensor is degraded. However, if at 612 it is determined that the outputs (e.g., SD test results) are not from the first completed SD test after an engine key-off event, then method 600 may continue to 616 which comprises not excluding the SD test result, and using the SD test result to determine if the NOx sensor is degraded, such as in the manner described above with reference to 322 of method 300 in FIG. 3. Method 600 then returns.

Thus, the method 600 at 608 comprises excluding SD test results from SD tests where the estimated and/or measured temperature of exhaust gasses sampled by the NOx sensor and/or flowing past the NOx sensor during the SD test is above a threshold, SD test results from SD tests where the estimated and/or measured oxygen concentration of exhaust gasses sampled by the NOx sensor during the SD test is below a first threshold or above a second threshold, and SD test results from the first SD test completed after an engine key-off event. Further, the method 600 may not comprise excluding SD test results from SD tests where the estimated and/or measured NOx concentration of exhaust gasses sampled by the NOx sensor during the SD test is above a threshold.

As such, the method 600 at 616 comprises only including SD tests results from SD tests where the estimated and/or measured temperature of exhaust gasses sampled by the NOx sensor and/or flowing past the NOx sensor during the SD test is below a threshold, SD test results from SD tests where the estimated and/or measured oxygen concentration of exhaust gasses sampled by the NOx sensor during the SD test is above a first threshold and below a second threshold, and SD test results from the first SD test completed after a first completed SD test after an engine key-off event.

In this way, the method may comprise excluding SD test results based on a set of qualification conditions. SD results that are excluded based on the qualification conditions may not be used to determine if the NOx sensor is degraded. Thus, SD tests results from SD tests that do not meet the qualification conditions may not be used to determine if the NOx sensor is degraded. The qualification conditions may include: SD tests results from completed SD tests after a first completed SD test after an engine key-off event, SD test results SD tests where the measured and/or estimated oxygen concentration of the exhaust gasses sampled by the NOx sensor during the SD test is between a lower first and higher second thresholds, and SD test results from SD tests where the measured and/or estimated temperature of exhaust gasses sampled by the NOx sensor during the SD test and/or flowing past the NOx sensor during the SD test is below a threshold. Further, in some examples, the qualification conditions may additionally include: SD tests results where the measured and/or estimated NOx concentration of exhaust gasses sampled by the NOx sensor during the SD test is below a threshold.

Thus, SD tests results from the first completed SD test result after an engine key-off event may be excluded from determining if the NOx sensor is degraded. Further, SD test results may be excluded if the estimated and/or measured temperature of exhaust gasses sampled by the NOx sensor and/or flowing past the NOx sensor during the SD test is above a threshold. SD test results from SD tests where the estimated and/or measured oxygen concentration of exhaust gasses sampled by the NOx sensor during the SD test is below a first threshold or above a second threshold may be excluded. Additionally or alternatively, the SD test results from SD tests where the estimated and/or measured NOx concentration of exhaust gasses sampled by the NOx sensor during the SD test is above a threshold may also be excluded.

In this way, a method may comprise determining if a NOx sensor is degraded based only on outputs from a NOx sensor during an SD test, and only if the outputs are generated from a completed SD test after a first completed SD test after an engine key-off event, where the estimated and/or measured temperature of exhaust gasses sampled by the NOx sensor and/or flowing past the NOx sensor during the SD test is below a threshold, the estimated and/or measured oxygen concentration of exhaust gasses sampled by the NOx sensor during the SD test is above a first threshold and below a second threshold, and in some examples, where the estimated and/or measured NOx concentration of exhaust gasses sampled by the NOx sensor during the SD test is below a threshold. Determining if the NOx sensor is degraded may include comparing a test result from the NOx sensor generated during a first mode of operation of the NOx sensor during the SD test to a lower first threshold, and a higher second threshold.

If the test result is greater than the higher second threshold or less than the lower first threshold, then it may be determined that the NOx sensor is degraded, and/or a vehicle operator may be notified. The first mode of operation of the NOX sensor may comprise reducing the oxygen concentration of exhaust gasses in a first chamber of the NOX sensor from a higher first level, to a lower second level in the second chamber. In some examples, the lower second level may be approximately $10^{-3}$ ppm. As such, in the first mode of operation of the NOx sensor, the concentration of NOx in the exhaust gasses may be measured and/or estimated based on a pumping current from a measuring electrode pair, where the electric potential applied across the measuring electrode pair may be sufficient to dissociate NOx molecules.

Thus, only qualified NOx sensor outputs, where the qualified NOx sensor outputs meet one or more qualification conditions, may be used to determine the NOx sensor is degraded. The qualification conditions may include a completed SD test after a first completed SD test after an engine-key off event, a temperature of exhaust gasses being below a threshold, a concentration of oxygen in the exhaust gasses being in-between lower first and higher second thresholds, and in some examples, a concentration of NOx in the exhaust gasses being lower than a threshold.

During engine operation where an engine is on, a reductant such as urea may be injected into an exhaust system upstream of an SCR catalyst. Together, the reductant and SCR catalyst may chemically reduce NOx molecules and therefore reduce NOx emissions. However, the urea injected during engine use and also urea droplets produced from a delivery line purging process may remain in the exhaust system after an engine key-off event. At exhaust temperatures above a threshold, the urea may be converted to $NH_3$. Ammonia may be registered by a NOx sensor in the exhaust system as NOx. Therefore, NOx levels estimated based on outputs from the NOx sensor may be overestimated when exhaust temperatures and/or urea levels exceed respective threshold levels. Further, because estimations and/or measurements of the NOx may vary due to different levels of urea and exhaust temperatures, NOx sensor that are degraded may not be diagnosed.

Specifically, NOx sensor may run a self-diagnostic (SD) test to in order to detect sensor degradation. However, high levels of urea and/or exhaust temperatures may reduce the accuracy of SD tests. Specifically, the ammonia produced by urea and high exhaust temperatures may be registered by the NOx sensor as NOx during the SD test. Accordingly, test results from separate SD tests of a NOx sensor that is not degraded may be as much or more different from one another than test results from SD tests of a NOx that is not degraded and test results from SD tests of a NOx sensor that is degraded. Therefore, NOx sensors that are degraded may not be distinguished and identified from NOx sensors that are not degraded. If a degraded NOx sensor is not identified, the accuracy of estimations of NOx levels may be reduced. As a result, degradation of the SCR catalyst and/or other components in the exhaust system used to control NOx emissions may fail to be detected, leading to increased NOx emissions.

However, a method may comprise determining if a NOx sensor is degraded based only on outputs from a NOx sensor during an SD test if a temperature of exhaust gasses is less than a threshold, and a concentration of NOx of the exhaust gasses is less than a threshold.

In this way, a technical effect of increasing the sensitivity and accuracy of detection of NOx sensor degradation is achieved by a method for determining if a NOx sensor is degraded based only on outputs from a NOx sensor during an SD test, and only if the outputs are generated from a completed SD test after a first completed SD test after an engine key-off event, where the estimated and/or measured temperature of exhaust gasses sampled by the NOx sensor and/or flowing past the NOx sensor during the SD test is below a threshold, the estimated and/or measured oxygen concentration of exhaust gasses sampled by the NOx sensor during the SD test is above a first threshold and below a second threshold, and the estimated and/or measured NOx concentration of exhaust gasses sampled by the NOx sensor during the SD test is below a threshold.

By excluding SD test results from SD tests where the exhaust gas temperature is greater than a threshold, and/or the oxygen concentration is outside the threshold range, and/or the NOx concentration is greater than a threshold, and/or the SD test is a first SD test after an engine key-off event, the variance in the SD test results may be reduced. As such, the sensitivity for distinguishing a degraded NOx sensor from a NOx sensor that is not degraded may be increased. Said another way, in the methods described herein, a higher percentage of NOx sensors that have become degraded may be detected than methods not excluding SD tests results based on exhaust temperature, NOx concentration, oxygen concentration, etc. Put more simply, a technical effect of improving the accuracy of outputs from a NOx sensor during a SD test is achieved by excluding SD test results in the manner described above. Thus, by improving the accuracy of SD test results, the efficiency in detecting a degraded NOx sensor may be increased. Therefore, the efficiency of a NOx emission control system in an exhaust system may be increased.

In this way, method may comprise: determining that a nitrogen oxide (NOx) sensor is degraded based on outputs received from the sensor via a CAN bus during a self-diagnostic (SD) test performed after a first completed SD test after a key-off event, only if the outputs are generated under conditions where a temperature at the sensor is less than a threshold, a NOx concentration is less than a threshold, and an oxygen concentration is within a threshold range. In some examples, the key-off event may comprise terminating a combustion cycle in an engine based on input from a vehicle operator via an input device. The outputs received from the NOx sensor, may in some examples be received via the CAN bus from a NOx control module, where the NOx control module may be in electrical communication with the NOx sensor.

Additionally, in some examples, the NOx concentration and oxygen concentration may be estimated based on outputs from the NOx sensor during the SD test. The temperature at the sensor may be based on outputs from a temperature sensor positioned in line with the NOx sensor relative to a flow of exhaust gasses past the NOx sensor. Additionally or alternatively, the method may comprise determining that the NOx sensor is degraded if the outputs of the SD test are not within a threshold range. In some examples, the threshold range may be determined based on the positioning of the NOx sensor relative to a selective catalytic reduction (SCR) catalyst. The outputs received from the NOx sensor may include SD tests results corresponding to the SD test, and where the SD test results may be a ratio between one or more pumping currents output by the NOx sensor and stored values. The method may in some examples additionally or alternatively comprise alerting a vehicle driver if it is determined that the NOx sensor is degraded. A completed SD test may comprise running the NOx sensor in both a first mode and a second mode, the second mode before the first mode, wherein the first mode may comprise adjusting the oxygen concentration in a cavity of the NOx sensor to a first level and measuring a concentration of NOx in the cavity, and wherein the second mode comprises adjusting the oxygen concentration in the cavity of the NOx sensor to a second level and not measuring a concentration of NOx in the cavity.

In another representation, a method may comprise: excluding a first completed self-diagnostic (SD) test result of a NOx sensor after an engine key-off event, excluding test results from a completed SD test if one or more of an exhaust gas temperature is greater than a threshold, an oxygen concentration of the exhaust gas is outside a threshold range, and a NOx concentration of the exhaust gas is higher than a threshold, otherwise not excluding test results from a completed SD test; and determining that the sensor is degraded only if the non-excluded test results are different from a reference value by more than a threshold. In some examples, the method may further comprise determining that an SD test is completed based on outputs from a NOx control module via a CAN bus, where the NOx control module may be in electrical communication with the NOx sensor. The exhaust gas temperature may be a temperature of exhaust gasses flowing past the NOx sensor during the SD test, and the temperature may be estimated based on outputs from a temperature sensor superposed with respect to the NOx sensor.

Additionally, the oxygen concentration and NOx concentration of the exhaust gas may in some examples be estimated based on outputs from the NOx sensor during the SD test. The method may additionally or alternatively comprise applying a correction factor to the test results based on a mean NOx concentration of the exhaust gas, where the mean NOx concentration is calculated based on the NOx concentration of the exhaust gas estimated over a duration, the duration being a portion of the SD test. In some examples, the method may additionally comprise supplying power to the NOx sensor from a glow plug control module, after the engine key-off event. Additionally or alternatively, the method may comprise receiving outputs from the NOx sensor via a NOx control module, where the outputs may comprise one or more of a status of an SD test, an SD test result, the oxygen concentration, and the NOx concentration. The method of claim 16, wherein the status of the SD test indicates whether or not the SD test has been completed.

In another representation, a system may comprise: a first NOx sensor positioned in an engine exhaust system upstream of a selective catalytic reduction (SCR) catalyst, a second NOx sensor positioned downstream of the SCR, a first temperature sensor aligned with the first NOx sensor relative to an exhaust gas flow in the exhaust system for measuring a temperature of exhaust gasses flowing past the first NOx sensor, a second temperature sensor aligned with the second NOx sensor relative to the exhaust gas flow in the exhaust system for measuring a temperature of exhaust gasses flowing past the second NOx sensor, and a controller in electrical communication with the first and second NOx sensor via a CAN bus, the controller having computer-readable instructions. The computer-readable may include instruction for determining that one or more of the first NOx sensor and second NOx sensor are degraded based on outputs from the first NOx and temperature sensor, and the second NOx and temperature sensors, respectively, where the outputs may be generated during a self-diagnostic test after a vehicle ignition key-off. A test result, test status, and one or more NOx concentrations and oxygen concentrations of exhaust gasses sampled by the NOx sensors may be estimated based on the outputs received from NOx sensors, and a temperature of exhaust gases may be estimated based on outputs received from the temperature sensors.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent code to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method comprising:
with an electronic controller communicating with a nitrogen oxide (NOx) sensor, determining that the NOx sensor measuring engine exhaust gas is degraded based on outputs received from the sensor during a self-diagnostic (SD) test performed after a first completed SD test after an ignition off event, only when the outputs are generated under conditions where the controller determines that a temperature at the sensor is less than a threshold, and an oxygen concentration is within a threshold range; and
generating a warning via a vehicle display responsive to the determination that the sensor is degraded.

2. The method recited in claim 1, wherein the determining that the NOx sensor is degraded is based further on outputs received from the sensor, only if the outputs are generated under conditions where a NOx concentration is less than a threshold.

3. The method recited in claim 1, wherein the ignition off event comprises terminating a combustion cycle in an engine based on input from a vehicle operator via an input device.

4. The method recited in claim 1, wherein the outputs received from the NOx sensor are received via a CAN bus from a NOx control module, where the NOx control module is in electrical communication with the NOx sensor.

5. The method recited in claim 1, wherein a NOx concentration and the oxygen concentration are estimated based on outputs from the NOx sensor during the SD test.

6. The method recited in claim 1, wherein the temperature at the sensor is based on outputs from a temperature sensor positioned in line with the NOx sensor relative to a flow of exhaust gasses past the NOx sensor.

7. The method recited in claim 1, further comprising determining that the NOx sensor is degraded in response to the received outputs of the SD test being outside a threshold range.

8. The method recited in claim 6, where the threshold range is determined based on the positioning of the NOx sensor relative to a selective catalytic reduction (SCR) catalyst.

9. The method recited in claim 1, wherein the outputs received from the NOx sensor are SD tests results corresponding to the SD test, and where the SD test results are a ratio between one or more pumping currents output by the NOx sensor and stored values.

10. The method recited in claim 1, further comprising alerting a vehicle driver in response to determining that the NOx sensor is degraded.

11. The method recited in claim 1, wherein a completed SD test comprises running the NOx sensor in both a first mode and a second mode, the second mode before the first mode, wherein the first mode comprises adjusting the oxygen concentration in a cavity of the NOx sensor to a first level and measuring a concentration of NOx in the cavity, and wherein the second mode comprises adjusting the oxygen concentration in the cavity of the NOx sensor to a second level and not measuring a concentration of NOx in the cavity.

12. A method comprising:
excluding a first completed self-diagnostic (SD) test result of a NOx sensor measuring exhaust gas after an engine ignition off event;
excluding second and subsequent test results from a completed SD test if one or more of an exhaust gas temperature is greater than a threshold, and an oxygen concentration of the exhaust gas is outside a threshold range;
otherwise not excluding second and subsequent test results from a completed SD test;
determining that the sensor is degraded only when the non-excluded test results are different from a reference value by more than a threshold; and
generating a warning via a display responsive to determining that the sensor is degraded.

13. The method of claim 12, further comprising determining that an SD test is completed based on outputs from a NOx control module via a CAN bus, where the NOx control module is in electrical communication with the NOx sensor.

14. The method of claim 12, wherein the exhaust gas temperature is a temperature of exhaust gasses flowing past the NOx sensor during the SD test, and where the temperature is estimated based on outputs from a temperature sensor positioned adjacent to the NOx sensor.

15. The method of claim 12, wherein the oxygen concentration of the exhaust gas is estimated based on outputs from the NOx sensor during the SD test.

16. The method of claim 12, further comprising applying a correction factor to the test results based on a mean NOx concentration of the exhaust gas, where the mean NOx concentration is calculated based on a NOx concentration of the exhaust gas estimated over a duration, the duration being a portion of the SD test.

17. The method of claim 12, further comprising supplying power to the NOx sensor from a glow plug control module, after the engine ignition off event.

18. The method of claim 12, further comprising receiving outputs from the NOx sensor via a NOx control module, where the outputs comprise one or more of a status of an SD test, where the status of the SD test indicates if the SD test is completed, an SD test result, the oxygen concentration, and a NOx concentration.

19. A system comprising:
a first NOx sensor positioned in an engine exhaust system upstream of a selective catalytic reduction (SCR) catalyst;
a second NOx sensor positioned downstream of the SCR;
a first temperature sensor aligned with the first NOx sensor relative to an exhaust gas flow in the exhaust system for measuring a temperature of exhaust gasses flowing past the first NOx sensor;
a second temperature sensor aligned with the second NOx sensor relative to the exhaust gas flow in the exhaust system for measuring a temperature of exhaust gasses flowing past the second NOx sensor; and
a controller in electrical communication with the first and second NOx sensors via a CAN bus, the controller having computer-readable instructions for:
determining that one or more of the first NOx sensor and second NOx sensor is degraded based on outputs from the first NOx and temperature sensors, and the second NOx and temperature sensors, respectively, where the outputs are generated during a self-diagnostic test after a vehicle ignition key-off, and generating a warning via a vehicle display responsive to the determination that the sensor is degraded.

20. The system recited in claim 19, wherein the controller further includes computer-readable instructions for a test result, test status, and one or more NOx concentrations and oxygen concentrations of exhaust gasses sampled by the NOx sensors to be estimated based on the outputs received from the first and second NOx sensors, and computer-readable instructions for estimating a temperature of exhaust gasses based on outputs received from the temperature sensors.

* * * * *